(12) United States Patent
Eckert et al.

(10) Patent No.: US 11,879,134 B1
(45) Date of Patent: Jan. 23, 2024

(54) RECOMBINEERING MACHINERY TO INCREASE HOMOLOGY DIRECTED GENOME EDITING IN THERMOPHILIC MICROBES

(71) Applicant: The Regents of the University of Colorado, a body, Denver, CO (US)

(72) Inventors: Carrie Eckert, Aurora, CO (US); Julie E. Walker, Wheat Ridge, CO (US)

(73) Assignee: The Regents of the University of Colorado, a body corporate, Denver, CO (US)

( * ) Notice: Subject to any disclaimer, the term of this patent is extended or adjusted under 35 U.S.C. 154(b) by 0 days.

(21) Appl. No.: 17/012,698

(22) Filed: Sep. 4, 2020

Related U.S. Application Data

(60) Provisional application No. 62/896,555, filed on Sep. 5, 2019.

(51) Int. Cl.
*C12N 15/90* (2006.01)
*C12N 9/22* (2006.01)
*C12N 15/11* (2006.01)

(52) U.S. Cl.
CPC ............. *C12N 15/902* (2013.01); *C12N 9/22* (2013.01); *C12N 15/11* (2013.01); *C12N 2310/20* (2017.05); *C12N 2800/80* (2013.01)

(58) Field of Classification Search
None
See application file for complete search history.

(56) References Cited

U.S. PATENT DOCUMENTS

2019/0360002 A1* 11/2019 Van Der Oost ...... C12N 15/902

OTHER PUBLICATIONS

Thermophiles, https://www.nps.gov/hosp/learn/thermophiles.htm, [retrieved Feb. 27, 2023] (Year: 2023).*
Thomason et al., Examining a DNA Replication Requirement for Bacteriophage λ Red- and Rac Prophage RecET-Promoted Recombination in *Escherichia coli*. mBio (2016), 7: e01443-16 (Year: 2016).*
Shuen Hon PhD Thesis, Reconstructing the ethanol production pathway of Thermoanaerobacterium saccharolyticum in Clostridium thermocellum, available Mar. 2018 (Year: 2018).*
Mougiakos et al., Next Generation Prokaryotic Engineering: The CRISPR-Cas Toolkit. Trends in Biotechnology (2016), 34: 575-587 (Year: 2016).*
Marks and Hamilton, Characterization of a thermophilic bacteriophage of Geobacillus kaustophilus. Arch Virol (2014), 159: 2771-2775 (Year: 2014).*
Harrington et al., A thermostable Cas9 with increased lifetime in human plasma. Nature Communications (2017), 8: 1424, pp. 1-8 (Year: 2017).*
Oh et al., CRISPR-Cas9-assisted recombineering in Lactobacillus reuteri. Nucleic Acids Research (2014), 42: e131, pp. 1-11 (Year: 2014).*
Acuña et al., Architecture and Gene Repertoire of the Flexible Genome of the Extreme Acidophile Acidithiobacillus caldus. PLOS One (2013), 8: e78237, pp. 1-15 (Year: 2013).*
GenBank: AEK57940.1, https://www.ncbi.nlm.nih.gov/protein/AEK57940.1, published Jan. 30, 2014 [retrieved Aug. 1, 2023] (Year: 2014).*
Genbank AEK57941.1, https://www.ncbi.nlm.nih.gov/protein/340556187, published Jan. 30, 2014, [retrieved Aug. 1, 2023] (Year: 2014).*

* cited by examiner

*Primary Examiner* — Samuel C Woolwine
*Assistant Examiner* — Catherine Konopka
(74) *Attorney, Agent, or Firm* — Michael M. McGaw; McGaw Law, P.C.

(57) ABSTRACT

A native Type I-B and heterologous Type II Clustered Regularly-Interspaced Short Palindromic Repeat/cas systems were developed and characterize to improve the ability to engineer *C. thermocellum* and other thermophilic microbes. The native Type I-B system was engineered for genome editing. For the Type I-B system, an engineered strain, termed LL1586, yielded 40% genome editing efficiency at the pyrF locus. When recombineering machinery was expressed the efficiency was increased to 71%. For the Type II GeoCas9 system, 12.5% genome editing efficiency was observed. When recombineering machinery was expressed, this increased to 94%. By combining the thermophilic CRISPR system (either Type I-B or Type II) with the recombinases, a new tool was developed that allows for efficient CRISPR editing. The tools provided herein enable CRISPR technologies to better engineer *C. thermocellum*, including engineering *C. thermocellum* for both increased lignocellulose degradation and biofuel production.

8 Claims, 10 Drawing Sheets

Specification includes a Sequence Listing.

Plasmid toxicity assay

*Not active; no cleavage/survival*

*Active; cleavage/death*

Chromosomal toxicity assay:

*Not active; no cleavage/survival*

*Active; cleavage/death*

*Cells killed = (CFUs NT strand − CFUs target strand)/(CFUs NT strand).
Negative values from the toxicity were assigned as 0.

RECOMBINEERING MACHINERY TO INCREASE HOMOLOGY DIRECTED GENOME EDITING IN THERMOPHILIC MICROBES

CROSS-REFERENCE TO RELATED APPLICATIONS

This application claims the benefit of U.S. Provisional Application No. 62/896,555, filed Sep. 5, 2019.

STATEMENT OF GOVERNMENT INTEREST

This invention was made with government support under grant number DE-AC05-000R22725 awarded by the U.S. Department of Energy. The government has certain rights in the invention.

REFERENCE TO AN ELECTRONIC SEQUENCE LISTING

The contents of the electronic sequence listing (0112-08-US1-PhotoconjugationReactions-Sequence _ST25v3.txt; Size: 6,476 bytes; and Date of Creation: Oct. 27, 2023) is herein incorporated by reference in its entirety.

BACKGROUND OF THE INVENTION

There are six types of CRISPR systems, including Type I and Type II CRISPR systems. Type I and Type II CRISPR systems have signature nucleases; Cas3 and Cas9, respectively. Both types encode cas1 and cas2 genes, which are involved in DNA acquisition. For Type I, the transcribed pre-crRNA is cleaved into repeat-protospacer-repeat units by Cash. In Type II, the pre-crRNA is cleaved by RNase III and the mature crRNA is complete upon addition of the small trans-activating RNA (tracrRNA). Type I systems have several proteins required for the interference step, while Type II systems only require the Cas9 nuclease for interference. In order to identify self vs. non-self during the interference stage, type I and type II Cas protein(s) recognize a specific nucleotide sequence termed a Protospacer Adjacent Motif (PAM). In Type I, a group of protein(s), termed the cascade, scan DNA for PAMs. Once a PAM is identified, the cascade proteins recruit the nuclease Cas3 to induce a ssDNA break. For type II, the Cas9-sgRNA ribonucleoprotein (RNP) scans for the PAM site and induces a dsDNA break adjacent to the PAM.

SUMMARY OF THE INVENTION

The robust lignocellulose-solubilizing activity of *Clostridium thermocellum* makes it a top candidate for consolidated bioprocessing for biofuel production. Genetic techniques for *C. thermocellum* have lagged behind model organisms, thus limiting attempts to improve biofuel production. To improve the ability to engineer *C. thermocellum* and other thermophilic microbes, native Type I-B and heterologous Type II Clustered Regularly-Interspaced Short Palindromic Repeat (CRISPR)/cas (CRISPR associated) systems were developed and characterized. The native Type I-B system was engineered for genome editing. Three thermophilic Cas9 variants (Type II) were tested. GeoCas9, isolated from *Geobacillus stearothermophilus*, was found to be active in *C. thermocellum*. CRISPR-mediated homology directed repair was employed to introduce a nonsense mutation into pyrF. For both editing systems, homologous recombination between the repair template and the genome appeared to be the limiting step. To overcome this limitation, three novel thermophilic recombinases were tested. The exo/beta homologs, isolated from *Acidithiobacillus caldus*, were observed to be are functional in *C. thermocellum*. For the Type I-B system, an engineered strain, termed LL1586, yielded 40% genome editing efficiency at the pyrF locus. When recombineering machinery was expressed the efficiency was increased to 71%. For the Type II GeoCas9 system, 12.5% genome editing efficiency was observed. Similar to the Type I-B system, when recombineering machinery was expressed for the Type II system, genome editing efficiency increased to 94%. By combining the thermophilic CRISPR system (either Type I-B or Type II) with the recombinases, a new tool was developed that allows for efficient CRISPR editing. The thermophilic recombineering tools provided herein enable CRISPR technologies to better engineer *C. thermocellum*, including engineering *C. thermocellum* for both increased lignocellulose degradation and biofuel production.

The present invention includes both one step and two step systems for engineering thermophilic bacteria. In certain embodiments of a two-step system, the system includes both a "repair" plasmid and a CRISPR "killing" plasmid. In the first step of the two-step system/process the thermophilic bacterial species is transfected with the repair plasmid. The repair plasmid can include a "repair template", which can be introduced into the thermophilic bacterial species genome through homologous recombination with the plasmid containing the repair template. The repair template will introduce a synonymous PAM mutation so the guide RNA can no longer recognize the target DNA. In a second step of the two-step process a killing plasmid is introduced into the bacteria. The killing plasmid can include Cas nuclease and guide RNA. If a repair template is present in the genome of bacteria receiving the second plasmid, the cells will survive cutting by the Cas nuclease. The integration of the repair template into the genome in the first step is greatly increased using a recombineering system. The two step system (or co-introduction of the plasmids containing the recombineering with the repair template and the CRISPR machinery with the guide RNA) is generally much more effective for most bacteria, but we now have all of the components for this system in *C. thermocellum*. An advantageous system is a two step system with the repair plasmid having the recombineering genes and a repair template, and the CRISPR "killing" plasmid with the Cas nuclease and/or guide RNA. A method for using the system can include the initial transformation of the repair plasmid followed by a second transformation with the CRISPR plasmid as a counterselection to remove unedited cells.

In a first aspect the present invention provides a kit for the engineering of a thermophilic bacterial species. The kit of the first aspect can include a first expression vector plasmid comprising a repair template and encoding recombineering machinery from a thermophilic bacterium including an exonuclease and a single-stranded DNA annealing protein and a second expression vector plasmid comprising an sgRNA and a thermophilic cas9 variant. In certain embodiments the exonuclease can be bacteriophage-derived Red recombinases (Exo or RecT). In certain embodiments the single-stranded DNA annealing protein is a Rac prophage recombinase (Beta or RecE). The thermophilic cas9 variant can be a variant selected from the group consisting of *Geobacillus stearothermophilus* (GeoCas9), *Acidothermus cellulolyticus* AAceCas9), and *Geobacillus thermodenitrificans* T12 (ThermoCas9). In an advantageous embodiment the thermophilic cas9 variant is a cas9 from *Geobacillus stearothermophilus* (GeoCas9). The thermophilic cas9 variant can further be nickase cas9. One or more strong constitutive promoters can be used on the second expression vector plasmid to drive transcription of the sgRNA and cas9. The kit according to the first aspect can further include a population of *Clostridium thermocellum* bacteria.

In a second aspect the present invention provides a second kit for the engineering of a thermophilic bacterial species. The kit of the second aspect can include a first expression vector plasmid comprising a repair template and recombinases and a second expression vector plasmid comprising an sgRNA and a thermophilic cas9 variant. The thermophilic cas9 variant can further be nickase cas9.

In a third aspect the present invention provides a third kit for the engineering of a thermophilic bacterial species. The kit of the third aspect can include a first expression vector plasmid comprising a repair template and recombinases and a second expression vector plasmid comprising an sgRNA and a Type I-B Cascade complex. The Type I-B Cascade complex can be a complex derived from *C. thermocellum*. The kit according to the third aspect can further include a population of *Clostridium thermocellum* bacteria.

In a fourth aspect the present invention provides a fourth kit for the engineering of a thermophilic bacterial species. The kit of the fourth aspect can include a first expression vector plasmid comprising a repair template and a second expression vector plasmid comprising an sgRNA and a thermophilic cas9 variant. The thermophilic cas9 variant can further be nickase cas9. In certain embodiments the kit according to the fourth aspect can further include one or more recombinases. In an advantageous embodiment the one or more recombinases are the exo/beta homologs from *Acidithiobacillus caldus*. The *Thermoanaerobacterium saccharolyticum* promoter #530 can be used to drive expression of the recombineering machinery. In further advantageous embodiments the cas9 is GeoCas9 derived from *Geobacillus stearothermpohilus*. In certain embodiments of the fourth aspect the Tsac_0068 promoter is used to drive expression of Cas9 and the strong *C. thermocellum* promoter Clo1313_2638 is used to drive expression of the sgRNA. The kit according to the fourth aspect can further include a population of *Clostridium thermocellum* bacteria.

In a fifth aspect the present invention provides a method of engineering a thermophilic bacteria population. The method can include the steps of (1) transfecting the bacteria population with a first expression vector plasmid comprising exo/beta recombineering genes derived from a thermophilic bacteria and a repair template, (2) performing one or more passages of the bacteria, whereby the passages allow for recombination between the repair template and the genome of bacteria in the bacterial population and (3) transfecting the bacteria population with a second expression vector plasmid comprising a CRISPR (Clustered Regularly Interspaced Short Palindromic Repeats)-associated protein 9 (Cas9) complex comprising an active thermophilic cas9-derived from *Geobacillus stearothermpohilus* (GeoCas9) and a guide RNA. In certain embodiments the population is a population of *Clostridium thermocellum* bacteria. The bacterial population can be passaged two or more times in selective media, three or more times in selective media, or four or more times in selective media. In an advantageous embodiment the recombineering genes are thermopile bacteria genus codon optimized exo/beta recombineering genes.

In a sixth aspect the present invention provides a composition having thermophilic *Clostridium thermocellum* bacteria, codon optimized recombineering exo/beta genes derived from *Acidithiobacillus caldus*, an active thermophilic cas9 derived from *Geobacillus stearothermpohilus* (GeoCas9), and a guide RNA.

BRIEF DESCRIPTION OF THE DRAWINGS

For a fuller understanding of the invention, reference should be made to the following detailed description, taken in connection with the accompanying drawings, in which:

FIG. 1 is a pair of drawings (FIGS. 1A and 1B) showing CRISPR/Cas genome editing in *C. thermocellum*.

FIG. 2 is a pair of diagrams (FIGS. 2A and 2B) and a graph (FIG. 2C) showing the toxicity assays.

FIG. 3 is a diagram (FIG. 3A) and graph (FIG. 3B) depicting recombineering machinery.

DETAILED DESCRIPTION OF THE PREFERRED EMBODIMENT

Members of the *Clostridium* genus have been studied for decades both as human pathogens and as industrial biocatalysts. Genetic techniques for *Clostridium* have lagged behind model organisms, thus hindering advances in our understanding of their physiology and metabolism. *Clostridium thermocellum* is an obligate thermophilic and anaerobic gram-positive bacterium that naturally ferments lignocellulose to ethanol and organic acids. *C. thermocellum* has recently been engineered to produce n-butanol.

Figure 1A:
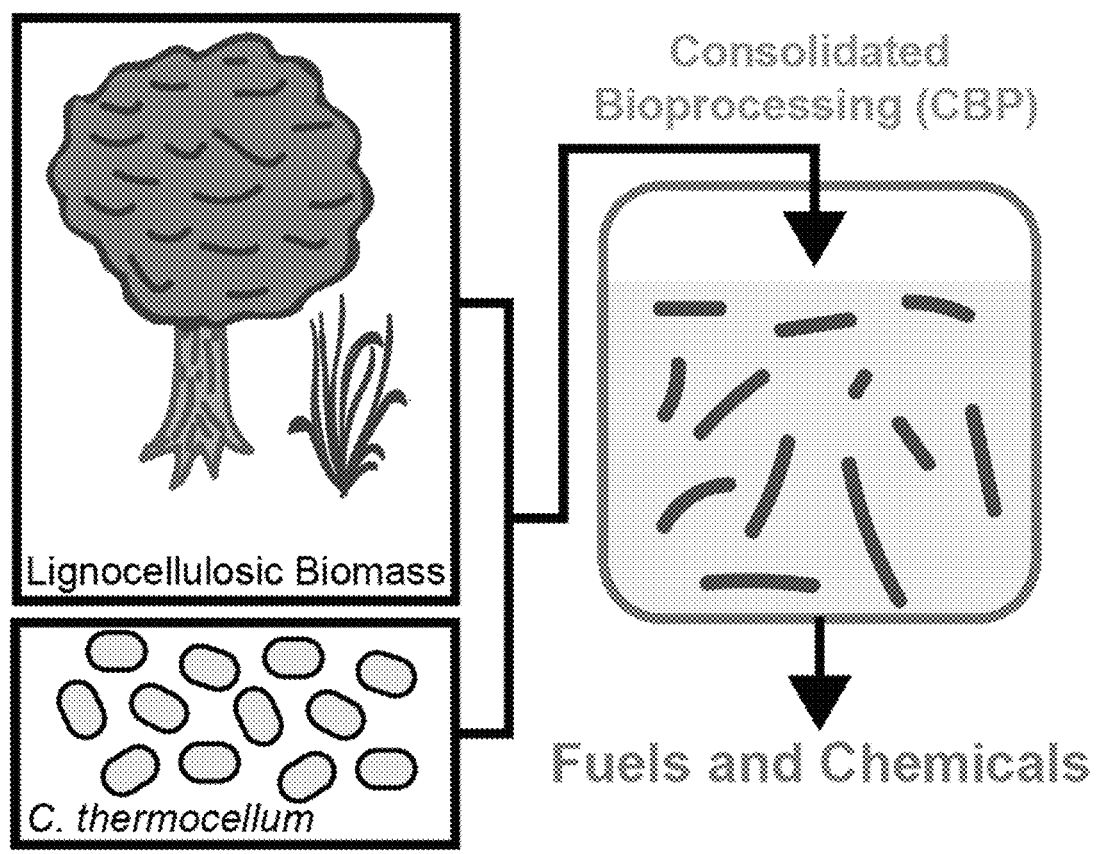
FIG. 1A is a drawing showing that *C. thermocellum* breaks down recalcitrant lignocellulosic biomass to produce biofuels. The robust lignocellulose activity of *C. thermocellum* make them a top candidate for consolidate bioprocessing.
Figure 1B:
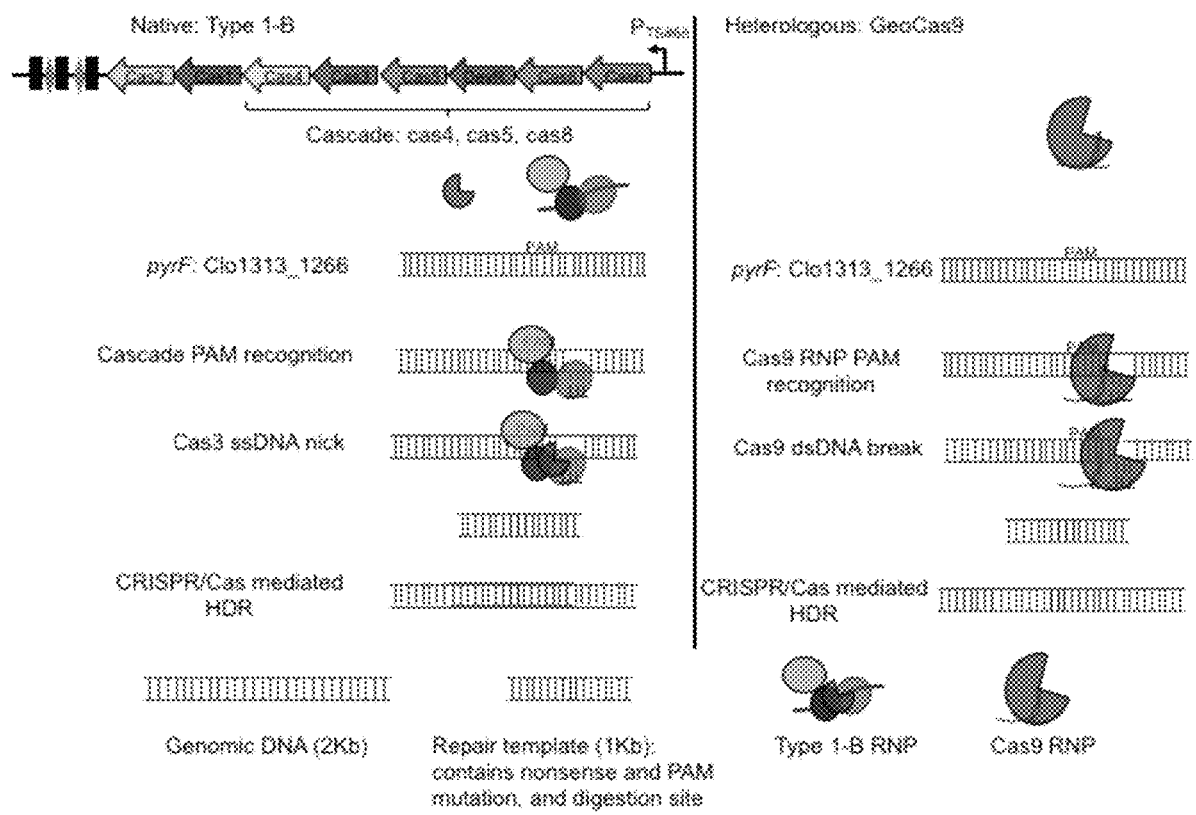
FIG. 1B is a schematic of the *C. thermocellum* native Type I-B operon (Clo1313_2969-2976) and heterologous Cas9 CRISPR/Cas genome editing systems.

The robust lignocellulose-solubilizing activity of *C. thermocellum* makes it a top candidate for consolidated bioprocessing for biofuel production (FIG. 1A). Established genetic techniques for *C. thermocellum* are laborious and introducing single nucleotide polymorphisms (SNPs) is difficult. Thus, efforts to increase the understanding of lignocellulose solubilization and biofuel production have been slow. Repurposing CRISPR (Clustered Regularly Interspaced Palindromic Repeats)/Cas (CRISPR associated) technology has revolutionized genome editing capabilities in a variety of biological systems, but has not been reported for *C. thermocellum*. To enable rapid genome engineering in *C. thermocellum*, both a heterologous Type II and a native Type I-B CRISPR/Cas genome editing system for *C. thermocellum* was developed (FIG. 1B).

There are six types of CRISPR systems, including Type I and II CRISPR systems. Type I and II CRISPR systems have signature nucleases; Cas3 and Cas9, respectively. Both types encode cas1 and cas2 genes, which are involved in DNA acquisition. For Type I, the transcribed pre-crRNA is cleaved into repeat-protospacer-repeat units by Cas6. In Type II, the pre-crRNA is cleaved by RNase III and the mature crRNA is complete upon addition of the small trans-activating RNA (tracrRNA). Type I systems have several proteins required for the interference step, while Type II systems only require the Cas9 nuclease for interference. In order to identify self vs. non-self during the interference stage, type I and II Cas protein(s) recognize a specific nucleotide sequence termed a Protospacer Adjacent Motif (PAM). In Type I, a group of protein(s), termed the cascade, scan DNA for PAMs. Once a PAM is identified, the cascade proteins recruit the nuclease Cas3 to induce a ssDNA break. For type II, the Cas9-sgRNA ribonucleoprotein (RNP) scans for the PAM site and induces a dsDNA break adjacent to the PAM.

Repurposing CRISPR/Cas technology allows for facile and marker-less strain construction. For CRISPR/Cas genome editing using homology directed repair, all that is required is an active single guide RNA (sgRNA), a Cas complex, and a repair template (also referred to as a homology arm). CRISPR/Cas-mediated homology directed repair enables the introduction of gene deletions, SNPs, and gene knock-ins, which were previously difficult to introduce, particularly in the case of SNPs. Due to the simplicity of the Type II (Cas9) system, it is the most commonly exploited system for genome engineering in model and non-model organisms. The simplicity is due to the dual tracrRNA: crRNA that was engineered to a single RNA chimera, thus only requiring Cas9 nuclease for genome editing. However, in many organisms, expression of a heterologous Cas9 is toxic and results in low transformation efficiency. In order to overcome Cas9 toxicity it is often necessary to control cas9/sgRNA expression through an inducible promoter. If inducible promoters have not been characterized, then another method has been to repurpose a prokaryote's native CRISPR/Cas system for genome editing.

Many prokaryotes have poor frequencies of homologous recombination. Expressing bacteriophage-derived k-Red recombinases (Beta/Exo) or Rac prophage recombinases (RecE/RecT) can increase CRISPR-mediated genome editing efficiencies ten-fold or more. Recombineering machinery includes an exonuclease (Exo or RecT) and a single-stranded DNA annealing protein (Beta or RecE) that facilitates homologous recombination between the repair template and the genome. Engineering highly efficient CRISPR/Cas9 genome editing systems often requires these recombinases.

Clostridial species often have low transformation efficiencies ($10^5$ CFU/μg DNA for *C. thermocellum*) and/or low rates of homology directed repair. Accordingly, establishing CRISPR/Cas systems has proven to be challenging. Implementing inducible cas9/sgRNA expression can facilitate high editing efficiencies. In some *Clostridium* species, expressing wild-type Cas9 (in the presence of a functional sgRNA) could be toxic, so a Cas9 nickase (Cas9n) variant was utilized. In Cas9n systems, one of the nuclease domains (either the HNH or RuvC domain) is inactivated. Thus, the RNP induces ssDNA breaks which are less lethal than dsDNA breaks. In these systems, inducing ssDNA breaks still increases the rate of homology directed repair at that genomic locus. However, the cell has time to incorporate the repair template or repair the ssDNA break before cell death occurs.

Many non-model organisms do not have a suite of characterized, inducible promoters to control a toxic, heterologous Cas9. In these prokaryotes, repurposing the native CRISPR array allows for genome editing. In both systems (Type I-B or II), low homologous recombination rates can often be a limiting step for genome editing. Recombineering machinery can be expressed to overcome this limitation. In addition, a "two plasmid" genome editing approach can be implemented. In this approach, the repair template is introduced first to the cell. Then, the CRISPR/Cas system is introduced to the cell and acts as a counter-selection that cuts and effectively kills all cells with genomes that are not edited. CRISPR/Cas9 mediated genome editing can be more efficient when Cas9 acts as a counter-selection post homologous recombination.

Many Cas9 systems use the Cas9 variant isolated from *Streptococcus pyogenes* (SpCas9). The SpCas9 is not active above 42° C. and cannot be used for genome editing in obligate thermophiles. Three thermophilic Cas9 variants have been characterized. The three variants are from *Geobacillus stearothermophilus*, *Acidothermus cellulolyticus*, and *Geobacillus thermodenitrificans* T12, and are referred to herein as GeoCas9, AceCas9, and ThermoCas9, respectively. Characterization of the thermophilic Cas9 variants furthers Cas9 genome editing in the obligate thermophile *C. thermocellum*.

Five CRISPR/Cas operons of the native Type I-B system have been shown in *Clostridium thermocellum*. However, only CRISPR locus 5 has a fully intact Type I-B CRISPR/Cas operon. Further in silico analysis of the Type I-B operon identified spacer-protospacer matches and putative PAM sequences. In addition, the Type I-B Cascade complex from *C. thermocellum* has been reconstituted and further characterized in vitro. Both a native Type I-B and a Type II (GeoCas9) CRISPR/Cas genome editing system in the thermophilic, industrially-relevant bacterium *Clostridium ther-* mocellum has been developed and is presented herein. In addition, the present invention provides newly-developed thermophilic recombineering machinery that will be useful in other obligate thermophiles.

Materials and Methods

Plasmids, strains and transformations: Table 1 describes the plasmids and strains. Plasmids were constructed using standard molecular biology techniques and Gibson cloning. Strains were constructed following the *C. thermocellum* strain construction protocol previously described or following the CRISPR/Cas editing technology described below. All transformations were carried out using previously described protocols [Olson, D. G. & Lynd, L. R. Transformation of *Clostridium thermocellum* by electroporation. *Meth. Enzymol.* 510, 317-330 (2012)].

Growth and selection conditions: Generally, for growth and selection conditions we used CTFUD rich media and used concentrations for selections as previously described [Olson, D. G. & Lynd, L. R. Transformation of *Clostridium thermocellum* by electroporation. Meth. Enzymol. 510, 317-330 (2012)]. Briefly, for experiments where pyrF was inactivated, 40 µg/mL of uracil was added to the medium to supplement for potential uracil auxotrophy from pyrF inactivation. For plasmid selection, with the exception of the second plasmid utilized in the two-step system, a selectable marker (gene encoding for CAT) was used that confers resistance to thiamphenicol. A concentration of 10 µg/mL of thiamphenicol was used for selection. The medium was supplemented with 250 µg/mL 5-FOA when utilizing the 5-FOA counter-selectable marker. For the two step/two plasmid system (described below) the second plasmid expressed a selectable marker that confers resistance to neomycin. For the Type I-B and Type II system various concentrations of neomycin had to be tested to find a concentration that was viable for cell growth, but did not have background. The optimal concentration of Neomycin was 150 µg/mL for the Type I-B system and 110 µg/mL for the Type II system (data not shown). Unless otherwise noted, the concentrations described were used in the CTFUD-rich medium, termed selective medium throughout this section.

PAM depletion assay: The CRISPR expression cassette plasmid pTY11B was amplified with ultramer pairs using Q5 polymerase. The forward ultramer in each pair contained the degenerate PAM library and spacer sequences being tested and the reverse ultramer contained the spacer expression cassette. The gel purified PCR product was Gibson assembled with the gblock XD824 and transformed into *E. coli* (NEB T7 express). An aliquot of the transformation mix was plated to determine library complexity and the remainder grown in 200 ml of LB/chloramphenicol and the plasmid DNA isolated for transformation of *C. thermocellum*. Three *E. coli* libraries were generated [pDGO180 (31nt spacer), pDGO182 (36nt spacer), pDGO183 (no spacer)] and used to transform *C. thermocellum* (LL1299 and LL1586) via electroporation with standard conditions. Following transformation cells recovered overnight at 50° C. and an aliquot plated to determine the number of transformants. The remainder used to inoculate a 50 ml culture of CTFUD+thiamphenicol(6 ug/ml), which was then grown at 55° C. for 24 hours. Three independent transformations were done for each plasmid library and strain of *C. thermocellum*. Plasmid DNA was isolated and this PAM depleted library DNA used for PCR with Illumina barcode primers to amplify the PAM/spacer region. The PCR product was column purified, concentrated (Zymo Research, DNA Clean and Concentrator) and used for Illumina sequencing followed by statistical analysis.

Illumina Sequencing and Analysis: Genome resequencing was performed as previously described [Zhou, J. et al. Physiological roles of pyruvate ferredoxin oxidoreductase and pyruvate formate-lyase in *Thermoanaerobacterium saccharolyticum* JW/SL-Y5485. *Biotechnol. Biofuels* 8, 138 (2015)]. Briefly, genomic DNA was submitted to the Joint Genome Institute (JGI) for sequencing with an Illumina MiSeq instrument. Unamplified libraries were generated using a modified version of Illumina's standard protocol. 100 ng of DNA was sheared to 500 bp using a focused ultrasonicator (Covaris). The sheared DNA fragments were size selected using SPRI beads (Beckman Coulter). The selected fragments were then end repaired, A-tailed, and ligated to Illumina compatible adapters (IDT, Inc) using KAPA-Illumina library creation kit (KAPA biosystems). Libraries were quantified using KAPA Biosystem's next-generation sequencing library qPCR kit and run on a Roche LightCycler 480 real-time PCR instrument. The quantified libraries were then multiplexed into pools for sequencing. The pools were loaded and sequenced on the Illumina MiSeq sequencing platform utilizing a MiSeq Reagent Kit v2 (300 cycle) following a 2×150 indexed run recipe. Paired-end reads were generated, with an average read length of 150 bp and paired distance of 500 bp. Raw data were analyzed using CLC Genomics Workbench, version 8.5 (Qiagen, USA). Reads were mapped to the reference genome (NC_017992). Mapping was improved by two rounds of local realignment. The CLC Probabilistic Variant Detection algorithm was used to determine small mutations (single and multiple nucleotide polymorphisms, short insertions and short deletions). Variants occurring in less than 90% of the reads and variants that were identical to those of the wild type strain (i.e., due to errors in the reference sequence) were filtered out. The fraction of the reads containing the mutation is shown in Table 7. To determine larger mutations, the CLC InDel and Structural Variant algorithm was run. This tool analyzes unaligned ends of reads and annotates regions where a structural variation may have occurred, which are called breakpoints. Since the read length averaged 150 bp and the minimum mapping fraction was 0.5, a breakpoint can have up to 75 bp of sequence data. The resulting breakpoints were filtered to eliminate those with fewer than ten reads or less than 20% "not perfectly matched." The breakpoint sequence was searched with the Basic Local Alignment Search Tool (BLAST) algorithm for similarity to known sequences. Pairs of matching left and right breakpoints were considered evidence for structural variations such as transposon insertions and gene deletions. Raw data is available from the JGI Sequence Read Archive.

Cas promoter characterization: LL1004, LL1299, LL1584, LL1585, LL1586, LL1587, LL1588 were grown in CTFUD at 55° C. and cells were collected at different stages of logarithmic growth and RNA prepared. 1 ml of bacterial culture was pelleted and lysed by digestion with lysozyme (15 mg/ml) and proteinaseK (20 mg/ml). RNA was isolated with an RNAeasy minikit (Qiagen #74104) and digested with TURBO DNase(Applied Biosystems) to remove contaminating DNA. cDNA was synthesized from 500 ng of RNA using the iScript cDNA synthesis kit (BioRad). qPCR reactions for each sample were performed in triplicate using cDNA with SsoFast EvaGreen Supermix (BioRad) at an annealing temperature of 55° C. to determine Cas6 (Clo1313_2976) and recA (Clo1313_1163) RNA levels. A gblock (IDT) containing the Cas6 and recA amplicons was used to generate a standard curve for each amplicon and Cas6 RNA levels were normalized to recA levels. Cas6 to recA levels at different growth stages for each strain were combined and averaged to determine Cas6 levels and relative promoter strength.

Single Guide RNA design: The terminology single guide RNA (sgRNA) is used throughout the text to describe the gRNA for both the Type I-B and Type II system. For the Type I-B system this refers to the crRNA that is processed to target pyrF. For the Type II system this refers to the single RNA chimera that is composed of the crRNA and the tracrRNA.

Type 1-B: Using the plasmid toxicity assay and PAM depletion library results, we designed guide RNAs by identifying a strong PAM site on the sense strand (PAM sequence: TTA) in the pyrF locus (Clo1313_1266) and then used the 37 basepair sequence immediately downstream as a target spacer (termed target sgRNA). As a control we identified a 37 basepair sequence on the sense strand in the pyrF locus without a predicted PAM site (PAM sequence: GGC) and used this for the non-target spacer (termed non-target sgRNA). In general, 37 bp spacers that were immediately downstream of strong predicted PAM sites were used for the target sgRNA; non-target sgRNA were the same length but lacked predicted PAM sites.

Type II: Single guide RNAs were designed using Benchling software. Briefly, using the CRISPR tool in benchling we assigned the guide type to single guide and the reference genome to ASM876v1 (*Clostridium acetobutylicum* ATCC 824). The guide length was set to 22, 24, or 20 and the PAM site was set to 5'-NNNNCRAA-3', 5'-NNNCC-3', or 5'-NNNNCNAA-3' for GeoCas9, AceCas9, and ThermoCas9, respectively. Only sgRNAs with 40-60% GC content were selected for further testing.

CRISPR/Cas toxicity assay: A toxicity assay was used to demonstrate functional DNA cutting for both the Type I-B and Type II systems. Differences in the systems required slightly different assay design (described below).

Type I-B: Two versions of the toxicity assay were used. The first characterized plasmid transformation efficiency following transformation of strains LL1299 or LL1586 (strain LL1299 with a strong promoter driving the Type I-B cas operon) with a plasmid containing a spacer expression cassette targeting various PAM/spacer combinations on the same plasmid. For this, the previously characterized autonomously replicating plasmid pMU102 was modified with a spacer expression cassette that used the Clo1313_1194 promoter to express the 37 bp spacer, 30 bp repeats, and terminator from CRISPR locus 4 adjacent to Clo1313_1653. The plasmid also contained the same spacer with various adjacent 5' PAM sequences. Transformations were employed as previously described and plated on rich medium with thiamphenicol. All transformations were done in biological duplicates and toxicity or percent of cells killed was calculated using the equation: (CFUs no PAM/spacer sgRNA+CFUs PAM/spacer sgRNA)/(CFUs no PAM/spacer sgRNA)*100.

The second assay characterized bacterial survival following transformation of strains LL1299 or LL1586 by a plasmid with or without (i.e., no sgRNA) a sgRNA targeting the Clo1313 pyrF locus. The plasmid used above was modified to include a ~1 kb pyrF repair template (repair template) and to express a sgRNA targeting the pyrF locus (the control omitted the sgRNA from the CRISPR expression cassette). All transformations were done in biological duplicates and toxicity results or percent cells killed was calculated using the equation: (CFUs no sgRNA+CFUs pyrF sgRNA)/(CFUs no sgRNA)*100.

Type II: The *Thermoanaerobacterium saccharolyticum* promoter #68 (ABC transporter) was used for expression of Cas9 and the previously characterized *C. thermocellum* promoter #2638 with a disrupted ribosome binding site was used to transcribe the sgRNA. The Cas9 variant and sgRNA were placed on the previously characterized autonomously replicating vector (pNW33N) to transform into *C. thermocellum* strain DSM1313 or LL1299.

For the toxicity assay, a non-target sgRNA and one to three target sgRNAs (termed target sgRNA) for each Cas9 variant were transformed to DSM1313. All target sgRNAs targeted the pyrF chromosomal coding region (Clo1313_1266). Transformations were employed as previously described and plated on CTFUD rich medium with 10 µg/mL thiamphenicol. All transformations were done in biological duplicates or triplicates and when more than one sgRNAs was tested then the combined average of CFUs for all sgRNAs was calculated. Toxicity results or percent cells killed was calculated using the equation: (CFUs non-target sgRNA−CFUs target sgRNA)/(CFUs non-target sgRNA)*100.

One step CRISPR/Cas genome editing in *C. thermocellum*: For one-step genome editing, the plasmid for each system was transformed to strain LL1299 and recovered in medium overnight at 51° C. The recovered transformation was plated on medium with thiamphenicol and uracil and incubated for 3-5 days at 53° C. If transformants were observed, ten colonies were pooled and grown up overnight in selective medium. To increase homologous recombination between the repair template and the genome, the cultures were passaged at a 1:20 dilution in selective medium. Passaging was repeated a total of five times. On the fifth passage, cultures were grown to mid-exponential, serially diluted and plated on selective medium+/−5-FOA. This was done for two or more biological replicates.

The effect of CRISPR (CRISPR fold change) for the one step method was determined using the equations below:

$$X(\text{increase in 5-FOA}^R \text{ phenotype}) = (\text{CFUs on Tm+5-FOA for target sgRNA or non-target sgRNA})/(\text{CFUs on Tm target sgRNA or non-target sgRNA})$$

$$\text{CRISPR fold-change for one step: } (X \text{ target sgRNA})/(X \text{ non-target sgRNA})$$

Type 1-B: The plasmid used in the toxicity assay was modified to include a ~1 kb repair template targeting the pyrF locus and introducing a stop codon and NheI digestion site in the region immediately 3' of a predicted PAM sequence. One version of the plasmid expressed a sgRNA targeting the pyrF locus at the site with the predicted PAM sequence and a second version expressed a control sgRNA that targeted the pyrF locus at a different site without a predicted PAM sequence. The one step plasmid with a target or non-target sgRNA was transformed into strain LL1586 (LL1299 with promoter Tsac_0068 driving cas operon expression) and recovered in CTFUD overnight at 50° C.

Type II: The plasmid used in the toxicity assay (Cas9 and non-target sgRNA/sgRNA #1) with the addition of a pyrF repair template introducing a stop codon, PAM mutation, and EcoR1 digest site was used for a one step genome editing approach (pJEW68 and pJEW69). In addition, a nickase GeoCas9 variant was constructed via Q5 site-directed mutagenesis (New England Biolabs'; catalog #: E0554S) wherein the catalytic domain was mutated at position H582A. The nickase Cas9 variant was sub-cloned into the vector containing the pyrF repair template and either a non-target or target sgRNA (pJEW84 and pJEW85, respectively) and tested using the one step genome editing approach.

Identification of thermophilic recombineering machinery: To identify thermophilic recombineering machinery, we searched all of the publicly available microbial genomes in the JGI IMG database using the "Genome Search by Metadata Category tool." We selected all genomes annotated as "thermophile" and searched for the presence of putative phage-type endonuclease (TIGRfam: TIGR03033; 27 hits). recT hits (21) and bet hits (1) were filtered for. Only genomes in which the recT or beta was directly adjacent to the recE or exo, respectively, were selected for further analysis. For recT/recE we filtered for bacteria that are gram positive, have an optimal temperature of at least 60° C. (optimal growth temperature of C. thermocellum) and are facultative anaerobes or anaerobes. The only beta/exo hit from Acidithiobacillus caldus (gene numbers: Atc1291 and Atc1292) and two recT/recE hits from Clostridium stercorarium (gene numbers: Cst0375 and Cst0374) and Geobacillus sp. (gene numbers: Geo2951 and Geo2953) were selected for testing.

Characterization of thermophilic recombinases in C. thermocellum: A codon optimized Gblock (Eurofins) was synthesized for each recombineering gene (see gene numbers above) and assembled via Gibson assembly on an autonomously replicating plasmid (pNW33N) containing a 1 kb pyrF repair template and thiamphenicol resistance. The Thermoanaerobacterium saccharolyticum promoter #530 (30S ribosomal protein S6) was used to drive expression of the recombineering machinery. Plasmids with and without the recombineering machinery were transformed to LL1299 and plated on medium with 6 μg/mL thiamphenicol and uracil. Transformants were observed for all plasmids (pJEW112, pJEW106, pJEW108) with the exception of the plasmid expressing recE/T from Clostridium stercorarium (pJEW107). Approximately 30 colonies were pooled from the transformation, grown up to mid-exponential phase, and serial dilutions for each culture were plated on selective medium+/−5-FOA. The percentage of colonies exhibiting homology-directed repair was determined by the number of colonies in the presence or absence of 5-FOA.

A two plasmid CRISPR/Cas genome editing system in C. thermocellum: For both systems (Type I-B and Type II), the repair template (repair template)+/−Atc recombineering machinery plasmids were transformed into strain LL1299. 10-30% of the recovered transformation was plated on medium with thiamphenicol and uracil and incubated for 3-5 days at 53° C. ~30 colonies were pooled and grown overnight in selective medium. To increase homologous recombination between the repair template and the genome, the cultures were passaged up to three times at a 1:20 dilution in selective medium. Genome editing was verified by restriction digest of a PCR amplicon covering the edit location. After two to three passages the culture was grown in 50 mL selective medium. The "killing vector" was transformed into a strain of LL1299 that already contained the repair template plasmid. 50-100% of the recovered transformation was plated on medium with Neomycin, uracil, +/−5-FOA. A subset of colonies were picked into selective medium (Type I-B) or medium supplemented with uracil (Type II). No neomycin selection was used when growing colonies for the Type II system due to technical difficulties with the Neomycin selection that are further described in the discussion.

The effect of CRISPR (CRISPR fold change) for the two plasmid method was determined using the equation below. Briefly, primers were designed wherein one primer annealed to the pyrF locus outside of the repair template and the second annealed to the repair template. Restriction enzyme, NheI or EcoR1 for Type 1-B and GeoCas9, respectively, was added to the PCR reactions and products were resolved on a 1% agarose gel. Note, the one-step and two-step protocol experimental differences required us to calculate CRISPR fold-change in slightly different ways.

CRISPR fold change for two step system: (% of checked edited colonies for the target sgRNA verified by restriction digest)/(% of checked edited colonies for non-target gRNA verified by restriction digest)

Type I-B: The plasmid pDGO186N-S1_nheI used for the one step protocol was modified and used for step-one of the two step protocol. The sgRNA expression cassette was removed leaving just the pyrF repair template in pDGO186NX-S1_nheI and in the case of pDGO186NXR-S1_nheI; the A. caldus exo/beta recombineering machinery was inserted and expressed in addition to the pyrF repair template. For step two of the protocol, pDGO186N-S1_nheI was modified by removing the pyrF repair template to generate sgRNA expression plasmids (killing' and control). The thiamphenicol resistance gene was replaced with the neomycin resistance gene. pDGO186N-CS3neo expressed the same target sgRNA as used in the one step protocol and pDGO186N-ContSneo the same control (non-target sgRNA) as in the one step protocol.

Type II: The same plasmids described in the "characterization of thermophilic recombineering machinery" section were used during step-one of the two step protocol. Briefly, one plasmid contained the 1 kb pyrF repair template (pJEW112) and another plasmid contained the 1 kb pyrF repair template and expressed A. caldus exo/beta recombineering machinery (pJEW106). The "killing vector" was similar to the plasmid previously described in the "CRISPR/Cas toxicity assay" section with the exception that the vector used for two step editing conferred neomycin resistance rather than thiamphenicol resistance. The "killing vector" conferred neomycin resistance and expressed GeoCas9 and a non-target or target sgRNA (pJEW117 and pJEW111 respectively).

Experiment 1—Type I-B Cas Operon and PAM Identification

Figure 5:
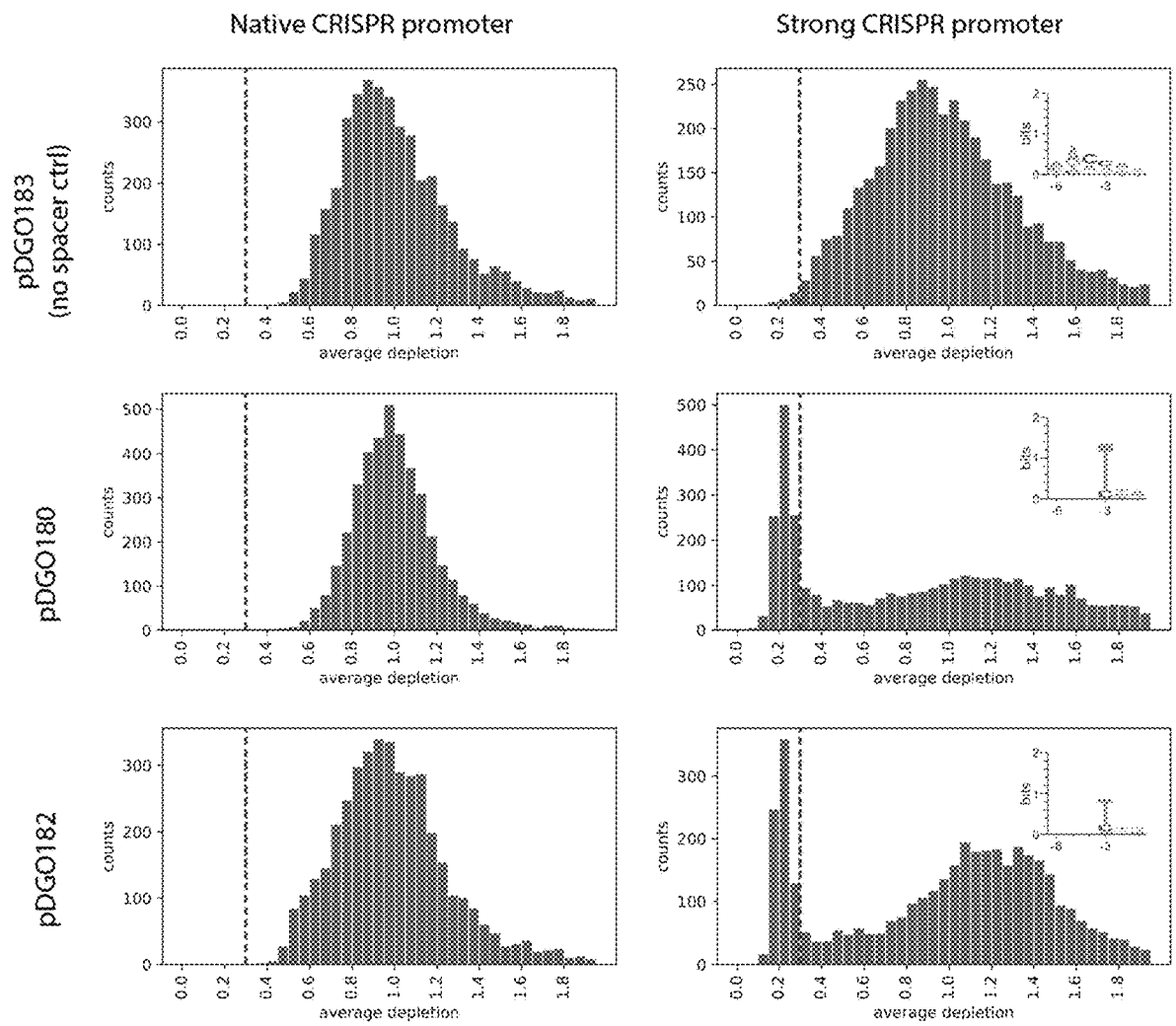
FIG. 5 is a set of graphs showing the results of PAM depletion assays. Depletion observed for pDGO180 and pDGO182 spacers, in the presence of a strong promoter. pDGO180 has a spacer from CRISPR locus 5. pDGO182 has a spacer from CRISPR locus 4. Average depletion of 1 means no depletion (i.e. no CRISPR-mediated killing). A bi-modal distribution is observed when CRISPR depletion worked. PAM sequences with depletion values of 0.3 or lower are predicted to be real PAM sequences.

Of the five CRISPR/Cas operons in Clostridium thermocellum only CRISPR locus 5 has a fully intact Type I-B CRISPR/Cas operon (Table 2). A first step in repurposing the Type I-B system at CRISPR locus 5 was identifying the PAM sequence. The approach to PAM identification was to identify the original sequence of the invading elements that ended up as CRISPR spacers in C. thermocellum, by BLAST search, as described by Pyne. From this analysis, the following PAM sequences were identified (5'-3'): CAGTTA, AATCCA, TTGTTA, AGGTTA, AGTTA, GATCA, and TAGTT. We tested these spacers using plasmid pTY #B/C (see Table 1), where the synthetic CRISPR array was driven by either the Clo1313_1194 promoter or the Clo1313_2638 promoter (FIG. 5). The synthetic CRISPR array on the plasmid is designed to target a second copy of the spacer elsewhere on the plasmid, such that a plasmid with a functional PAM sequence will cause itself to be cut by Cas3 and will be unable to provide antibiotic resistance to the cell. Thus, functional PAM sequences might lead to reduced transformation efficiency. In the presence of a strong promoter (Clo1313_1194 or 2638), and with PAM sequences 5'-CAGTTA-3' and 5'-GATCA-3' a 10-fold decrease in transformation efficiency (from $5 \times 10^4$ to $<5 \times 10^3$ CFU/ug DNA) was observed, indicating that CRISPR-mediated interference was occurring.

To further characterize the specific PAM sequence, a PAM depletion assay was performed. A library of all 4096 possible 6 bp PAM sequences was built, transformed into *C. thermocellum*, and the sequences that were subsequently depleted from the library were identified. It was observed that the base pairs at the −6,−5 and−4 positions were unimportant. Of the remaining 81, 3 bp PAM sequences, 10 showed strong depletion with both spacers (Table 3) and can be summarized by the degenerate sequences 5'-TTN-3' and 5'-TNA-3 '.

Experiment 2—Toxicity Assay to Determine CRISPR/Cas Activity

*C. thermocellum*, like most bacteria, does not encode for proteins responsible for non-homologous end joining. Thus, a single or double-strand DNA break caused by an active Cas:sgRNA RNP complex cannot be repaired under normal circumstances. A toxicity assay was used wherein the Cas: sgRNA RNP complex targets either a plasmid or the chromosome for cleavage (FIG. 2). If the RNP is active then cleavage will occur destroying a plasmid that confers resistance to an antibiotic (FIG. 2A), or the chromosome (FIG. 2B) will be targeted for a ss/dsDNA break causing cell death.

Figure 2A:
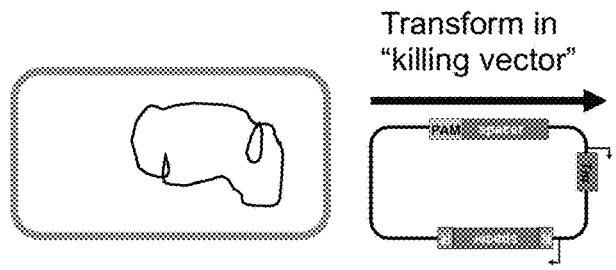
FIG. 2A is a diagram illustrating a toxicity assay wherein the RNP targets the transformed plasmid. If the RNP is active then cleavage of the plasmid will occur destroying the plasmid conferring resistance to the selection.
Figure 2A:
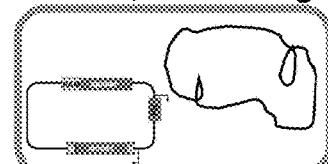
Figure 2A:
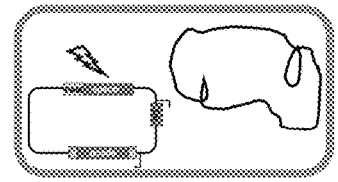
Figure 2B:
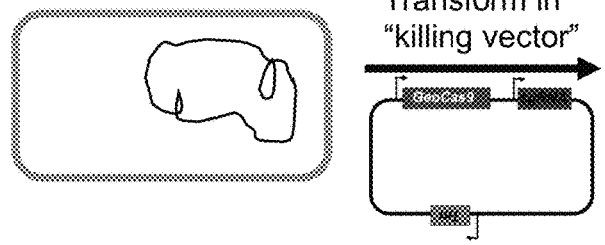
FIG. 2B is a diagram illustrating a toxicity assay wherein the RNP targets the chromosome. If the RNP is active then cleavage of the chromosome will occur resulting in cell death.
Figure 2B:
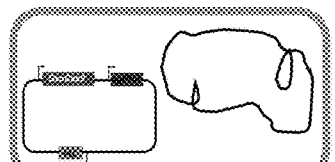
Figure 2B:
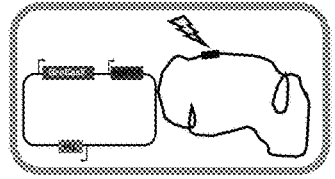
Figure 2C:
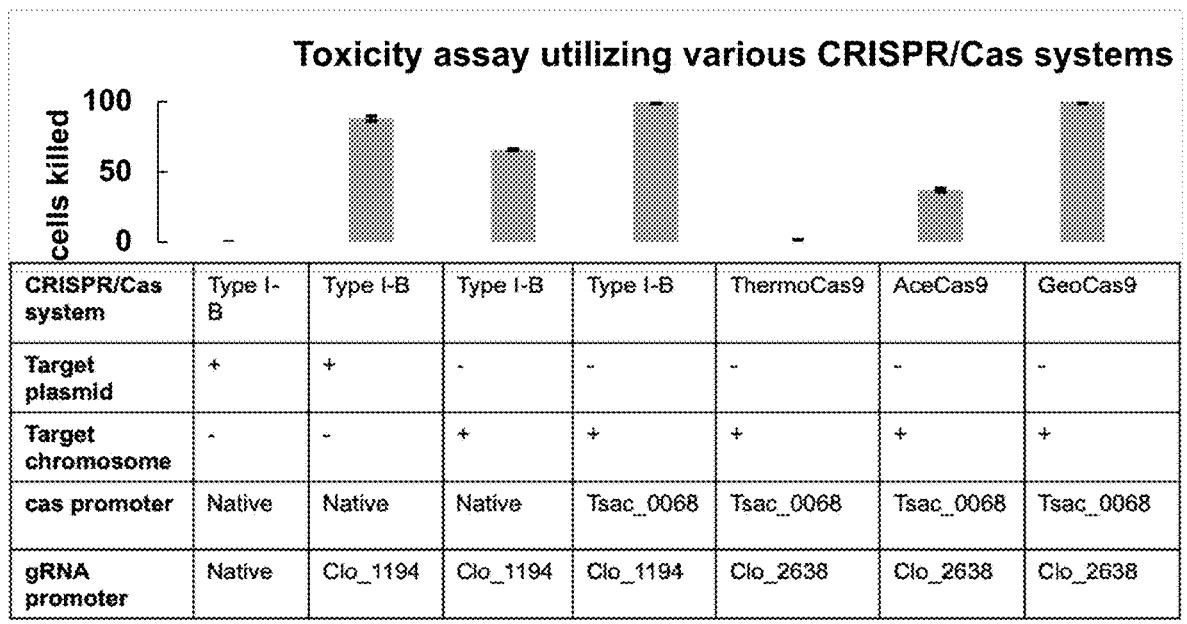
FIG. 2C is a graph showing the results of the toxicity assay for various systems tested.

The activity of the Type I-B system was tested by designing a plasmid that expresses the sgRNA (repeat-spacer-repeat) such that the RNP targets the same plasmid. For all cases, we used the PAM sequence 'TTA' (full PAM sequence: 5'-CAGTTA-3') and tested several spacers targeting the plasmid. Constructs without a spacer were used as a negative control. When the endogenous cas operon promoter, and spacer array promoter were used no cell killing was observed. We hypothesized that expression of the sgRNA was too low for killing, so we used a strong constitutive promoter, Clo1313_1194, to drive expression of the sgRNA. Swapping out the native spacer array promoter for the stronger promoter Clo1313_1194 resulted in 88% cell killing (FIG. 2C).

Figure 6:
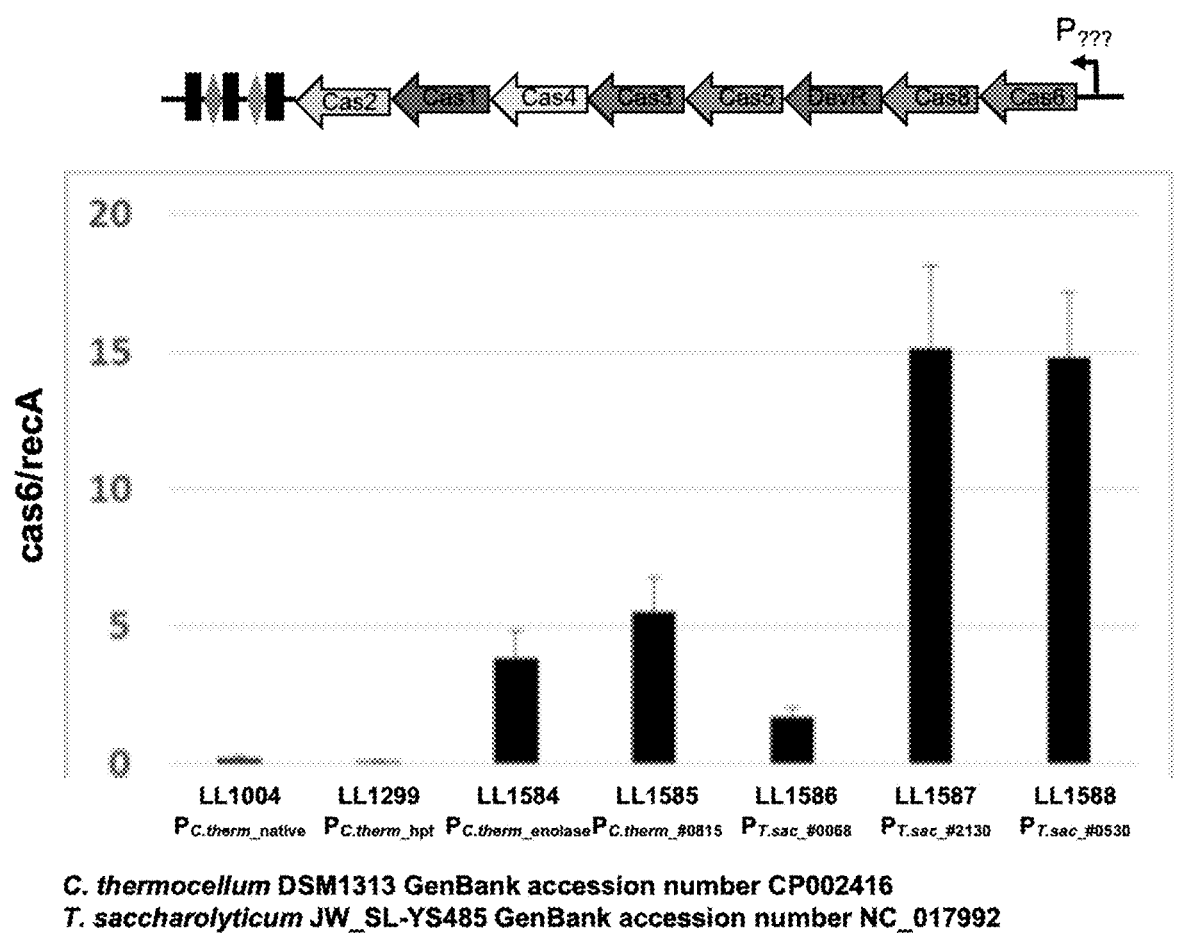
FIG. 6 is a graph showing the results of Cas promoter characterization. Five different promoters were placed directly upstream of the cas operon. Promoter strength was determined by comparing expression levels of cas6/recA between each strain.

Once the Type I-B system was confirmed to be active, the activity of the RNP when targeting the chromosome rather than a plasmid was tested. A spacer targeting the chromosomal pyrF locus (Clo1313_1266) was tested using the same system as described above (i.e., native promoter to drive cas expression and Clo1313_1194 promoter to drive sgRNA expression), and 65.8% cell killing was observed (FIG. 2C). Ideally, 100% cell killing is desired so there is minimal to no background when employing genome editing as Cas cleavage should act as a counter-selection. To further improve the efficiency of CRISPR-mediated DNA cleavage, five promoters were tested for upregulation of the cas operon (Clo1313_2969-2976). These promoters included two from *C. thermocellum* (enolase and 0815), and three from *Thermoanaerobacterium saccharolyticum* (Tsac_0068, 0530, 2130). Of these, the Clo1313_0815 and Tsac 0068 promoters gave the most reliable results (FIG. 6). We chose the Tsac 0068 promoter because it is not present in the *C. thermocellum* genome (and thus is not a target for unwanted homologous recombination). The resulting strain was named LL1586 and was able to achieve 99.8% cell killing in our toxicity assay.

Three thermophilic Cas9 variants, termed ThermoCas9, AceCas9, and GeoCas9, have been characterized. We employed a toxicity assay to test the activity of all three thermophilic Cas9 variants in *C. thermocellum*. Similar to the design of the Type I-B system, we used the Tsac 0068 promoter to drive expression of Cas9 and the strong *C. thermocellum* promoter Clo1313_2638 to drive expression of the sgRNA. For this assay, we targeted the pyrF locus. Two to three sgRNAs were designed for each thermophilic Cas9 variant and one non-target sgRNA was designed as a negative control. For ThermoCas9 no cell killing was observed, for AceCas9 37% cell killing was observed, and for GeoCas9 100% cell killing was observed (FIG. 2C). We speculate that the Cas9 variant could be misfolding in *C. thermocellum* or the sgRNAs tested may not be effective sgRNAs. Nonetheless, for GeoCas9 all three sgRNAs tested resulted in 100% cell death whereas ~150 CFUs were obtained for the non-target sgRNA control. Based on these results, the GeoCas9 variant was selected for evaluating CRISPR/Cas9-mediated homology-directed repair (HDR).

In summary, the toxicity assay demonstrated a highly active engineered Type I-B CRISPR/Cas system and a highly active Type II GeoCas9 system (Table 4). Making the Type I-B system functional required identifying the correct PAM sequence and placing strong constitutive promoters upstream of both the chromosomal cas operon and the plasmid-encoded sgRNA. Making the Type II system functional required identification of a thermostable Cas9 protein and putting strong promoters in front of both the cas9 gene and sgRNA. We are now poised to introduce a repair template for CRISPR/Cas mediated homology directed repair.

Experiment 3—a One-Step CRISPR/Cas Genome Editing System—Effectiveness and Efficiency We targeted the pyrF gene (Clo1313_1266) for inactivation because the resulting mutants can easily be identified by their resistance to the toxic uracil analog 5-fluoroorotic acid (5-FOA). Furthermore, deletion of pyrF has no fitness defect for *C. thermocellum* when the media is supplemented with uracil. Based on previous reports, we expect some background level of 5-FOA resistance due to spontaneous pyrF point mutations; however, this should be the same for the non-target and target sgRNAs, and thus not interfere with measurements of CRISPR effectiveness/fold-change. For both systems, a pyrF repair template was designed containing a nonsense mutation to inactivate pyrF function, a unique restriction site to facilitate verification of the modification, and a mutation in either the PAM or spacer region to prevent subsequent editing by the RNP complex. The repair template was included on the same plasmid as the sgRNA.

For the Type II GeoCas9 system, ~50 CFUs were observed from the transformation with the non-target sgRNA; however, no CFUs were observed when the target sgRNA was transformed (Table 5). We predicted that Geo-Cas9 was inducing dsDNA breaks and killing cells before homology-directed repair could occur. Other CRISPR/Cas genome editing systems have overcome the high toxicity of Cas9-mediated DNA cleavage by controlling cas9 gene expression with an inducible promoter. To attempt to overcome the Cas9 toxicity, we used a recently characterized thermophilic riboswitch to control geoCas9 expression; however, no CFUs were observed (data not shown). We predict that the Cas9 RNP is extremely potent, and thus even leaky expression of Cas9 from the inducible riboswitch is enough to kill cells.

Another way to overcome Cas9 toxicity is by using a nickase Cas9 (Cas9n) variant wherein one of the cleavage sites is mutated thus inducing ssDNA breaks rather than dsDNA breaks. A GeoCas9n variant, GeoCas9H582A, was tested using the one step system. For the GeoCas9n, when plated without 5-FOA, ~200 CFUs were observed with the non-target sgRNA and ~150 CFUs were observed from the target sgRNA (Table 5). For the type 1-B system, using the engineered strain, LL1586, ~18,000 CFUs were observed for the non-target sgRNA and ~7 CFUs were observed for the target sgRNA. However, none of the colonies screened (in either system) showed signs of editing. In addition, neither system showed phenotypic evidence of CRISPR-based pyrF inactivation (i.e. an increase in 5-FOA resistant colonies).

It has been noted in CRISPR/Cas genome editing for other Clostridial organisms that serial transfer in liquid media increased the number of edited genomes. We speculate that this is required due to insufficient homology-directed repair. To increase the occurrence of homology-directed repair we employed serial transfers. After five rounds of serial transfer, we measured CRISPR-based editing based on 5-FOA resistance. For both Type I-B and Type II editing efficiencies were very low for both target and non-target sgRNA. CRISPR fold-change was 7.3 fold above background (i.e., non-target sgRNA) for the Cas9n system, and 1.3-fold above background for the Type I-B system (Table 5).

In both systems, CRISPR/Cas increased genome editing efficiencies; however, the overall editing efficiency was too low for practical use as a genome editing tool. In addition, for the Cas9n system, the non-target sgRNA and target sgRNA had similar transformation efficiencies showing that ssDNA nicks cannot be used as a counter-selectable marker. In order to use the Type II (Cas9) system as a counter-selection we predicted it would be necessary to use the wt Cas9 which makes dsDNA breaks. On the other hand, for the Type I-B system the transformation efficiency for the target sgRNA was ~10,000× lower than the non-target sgRNA, indicating that the Type I-B system can be used as an effective counter-selection.

Experiment 4—Type I-B Escape Mutants Correlated with Point Mutations in Cas Genes To better understand the appearance of the Type I-B escape mutants (i.e. colonies transformed with a target sgRNA, but that still had the wild type sequence at the pyrF locus), total DNA (genomic and plasmid) was re-sequenced from seven mutants. In all cases, we observed a mutation in one of the genes in the cas operon (specifically cas3, cas5 or cas8) that would be expected to inactivate the encoded protein (Table 3). We did not observe any mutations in the plasmid sequence. Although the plasmid replicon is known to support copy numbers of 10-1000 in C. thermocellum, our resequencing data unexpectedly showed that plasmid copy number was approximately one.

Figure 3A:
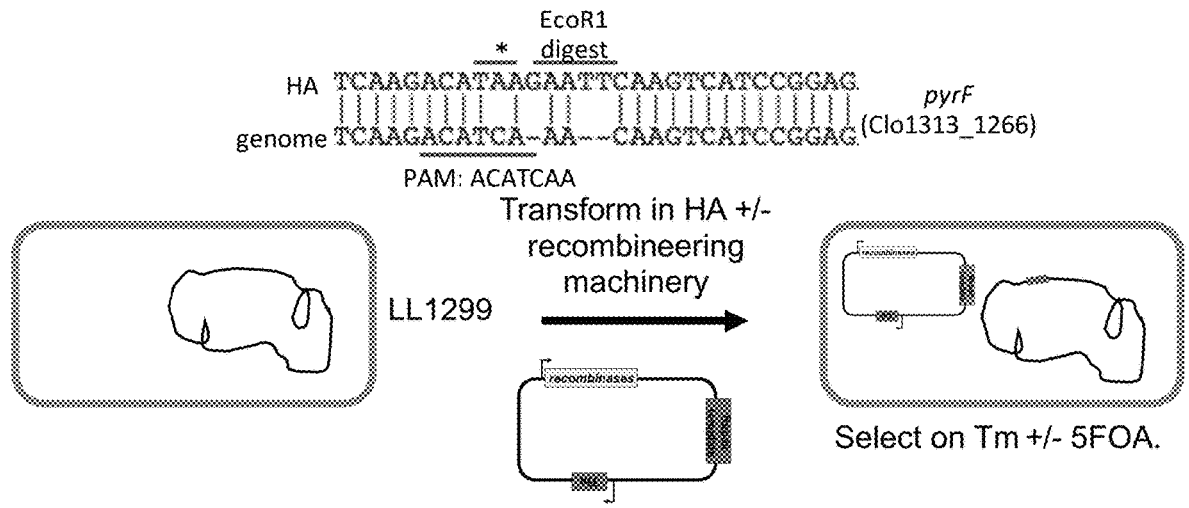
FIG. 3A is a diagram showing a pictorial description of the repair template [SEQ ID NO. 30] used to test the recombineering machinery on a target sequence [SEQ ID NO. 31]. Schematic for experimentally determining percent homology directed repair.

Experiment 5—a Recombineering System Overcomes Limitations of Homology-Directed Repair in C. thermocellum The combination of high cutting efficiency (from the killing assay) and low genome editing efficiency (from the one-step editing protocol) indicated that homology directed repair was the rate limiting step. To improve the rate of homologous recombination, we identified thermophilic recombinases (e.g. beta/exo from k-Red or recE/recT from Rac prophage). Three recombineering machinery pairs were tested in C. thermocellum: beta/exo isolated from Acidithiobacillus caldus (Atc), recE/recT isolated from Clostridium stercorarium (Cse) and recE/recT isolated from Geobacillus sp (Geo) (FIG. 3).

Figure 3B:
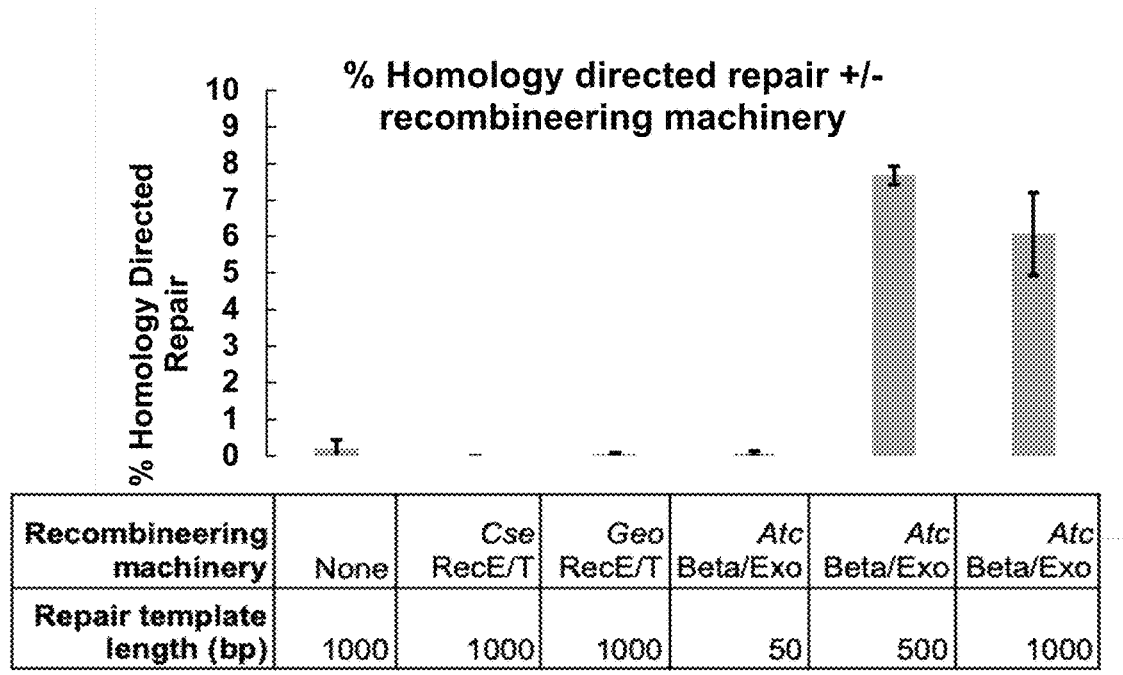
FIG. 3B is a graph showing percent homology directed repair that was determined using recombineering machinery isolated from three thermophilic organisms. Cse denotes *Clostridium stercorarium*, Geo denotes *Geobacillus sp*, and Atc denotes *Acidithiobacillus caldus*. Various repair template lengths (1000, 500 and 50 bp) were tested for the active recombineering machinery isolated from *A. caldus*.

Recombineering plasmids containing the same pyrF repair template used for CRISPR/Cas9 genome editing and expressing each pair of recombineering genes were transformed into C. thermocellum (strain LL1299). Interestingly, no colonies were obtained for Cse recE/T, indicating toxicity of C. stercorarium recombinases in C. thermocellum. For the other pairs of recombinases, sufficient numbers of colonies were obtained to assay for changes in homology-directed repair (HDR). Approximately 30 colonies were pooled, sub-cultured, and plated with and without 5-FOA to measure changes in the rate of pyrF mutation due to HDR. The Geo recE/T recombinases did not show any change in HDR (FIG. 3B). By contrast, the Atc recombinases showed a 35-fold increase in HDR compared to baseline homologous recombination. Further experiments showed that for Atc, the length of the repair template can be decreased from 1000 bp to 500 bp with no effect on HDR (FIG. 3B). This technology will be transferable to other industrially relevant thermophilic organisms.

Figure 4A:
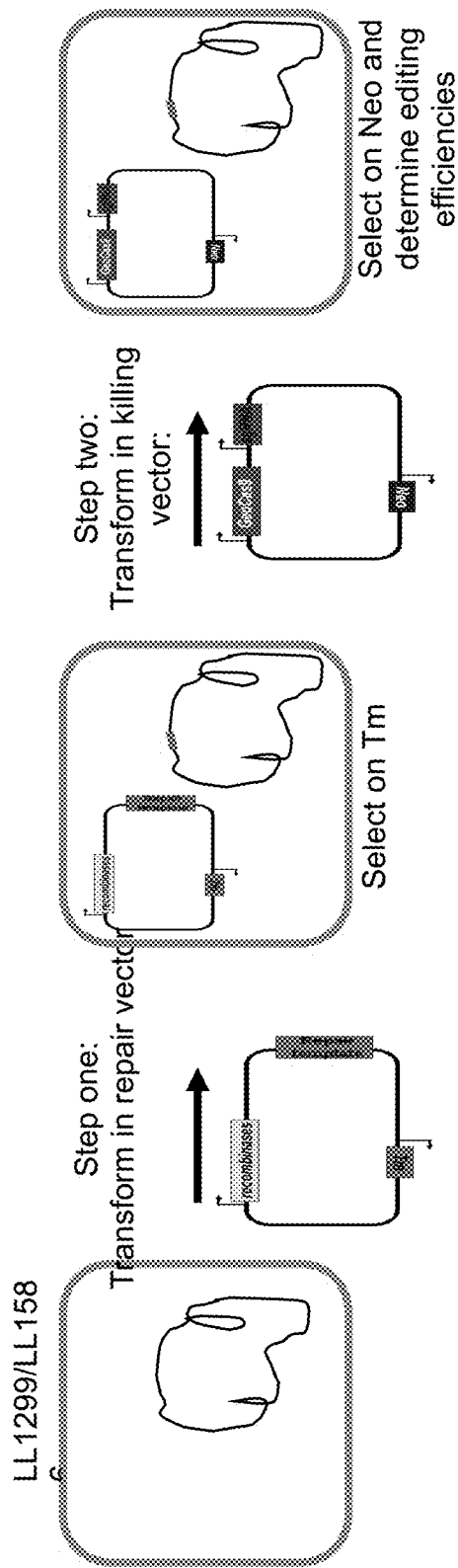
FIG. 4A is a diagram providing a schematic for two-step CRISPR/Cas genome editing.

Experiment 6—Efficient Genome Editing Using a Two-Step CRISPR/Cas, Recombineering System Due to the low editing efficiency of the one-step CRISPR/Cas system, a two-step genome editing approach was developed. The first step involves transforming cells with a "repair" plasmid containing the repair template and (optionally) recombinases (e.g. A. caldus exo/beta homologs). A certain fraction of the population will incorporate the repair template onto the genome. The second step involves transforming the cells with a second plasmid containing the CRISPR machinery (sgRNA, and cas9 for the Type II system). The second "killing" plasmid is used as a counter-selection to kill cells that were not edited by the first plasmid (FIG. 4A).

In C. thermocellum, two antibiotic resistance markers (cat and neo) and two origins of replication (pNW33N and pBAS2) have been characterized. However, the two plasmid origins have different temperature sensitivities that makes them incompatible (data not shown). Thus, a pNW33N origin of replication was used for both plasmids, but both of them were maintained simultaneously by using different antibiotic resistance markers for each one: cat for the "repair" plasmid and neo for the "killing" plasmid.

After transformation with the "repair" plasmid, cells were grown for about 13 generations (3 passages of 1:20 dilution) to allow time for recombination to occur. Since pyrF was used as a reporter, the frequency of repair was measured either by plating on 5-FOA (which would measure the sum of pyrF mutations due to homologous recombination and due to random point mutations) (FIG. 3) or by transforming with a "killing" vector and measuring changes in transformation efficiency (which would measure the sum of pyrF mutations due to homologous recombination and "escape" mutations in other parts of the CRISPR machinery) or by doing both. This third option (transforming with a "killing" vector and selection on 5-FOA) resulted in no transformants, so the second option ("killing" vector only) was used, and subsequently verified the presence of the target mutation by PCR and restriction digest.

Figure 7:
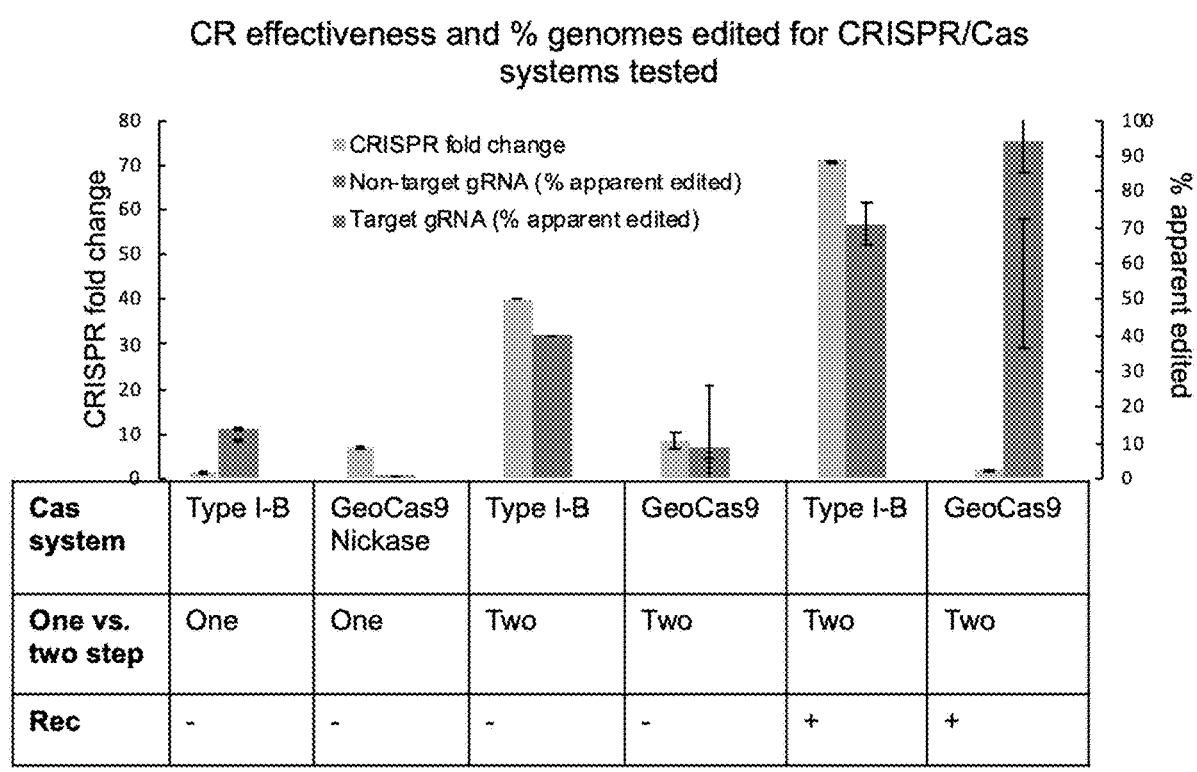
FIG. 7 is a graph showing a summary of CRISPR fold change and percent genomes edited for the various CRISPR/Cas systems tested.

All combinations of CRISPR targeting (target vs. non-target control), CRISPR system (Type I-B vs II), and recombinase (+/−), were evaluated in biological duplicates (Table 6 and FIG. 7). In the absence of a recombinase, less than 1% of the cells would be expected to survive the "killing" plasmid (FIG. 3). Instead, 20-50% survival was observed for the Type I-B system and >100% for the Type II system. In the presence of a recombinase, 5-10% of the cells would be expected to survive the "killing" plasmid. Again, much higher survival was observed, with 10-30% for the Type I-B system and 50-60% for the Type II system. One possible explanation for the increased survival is a large contribution from escape mutants. Another possibility is that the "killing" plasmids actually interact with the "repair" plasmids to stimulate recombination.

Figure 4B:
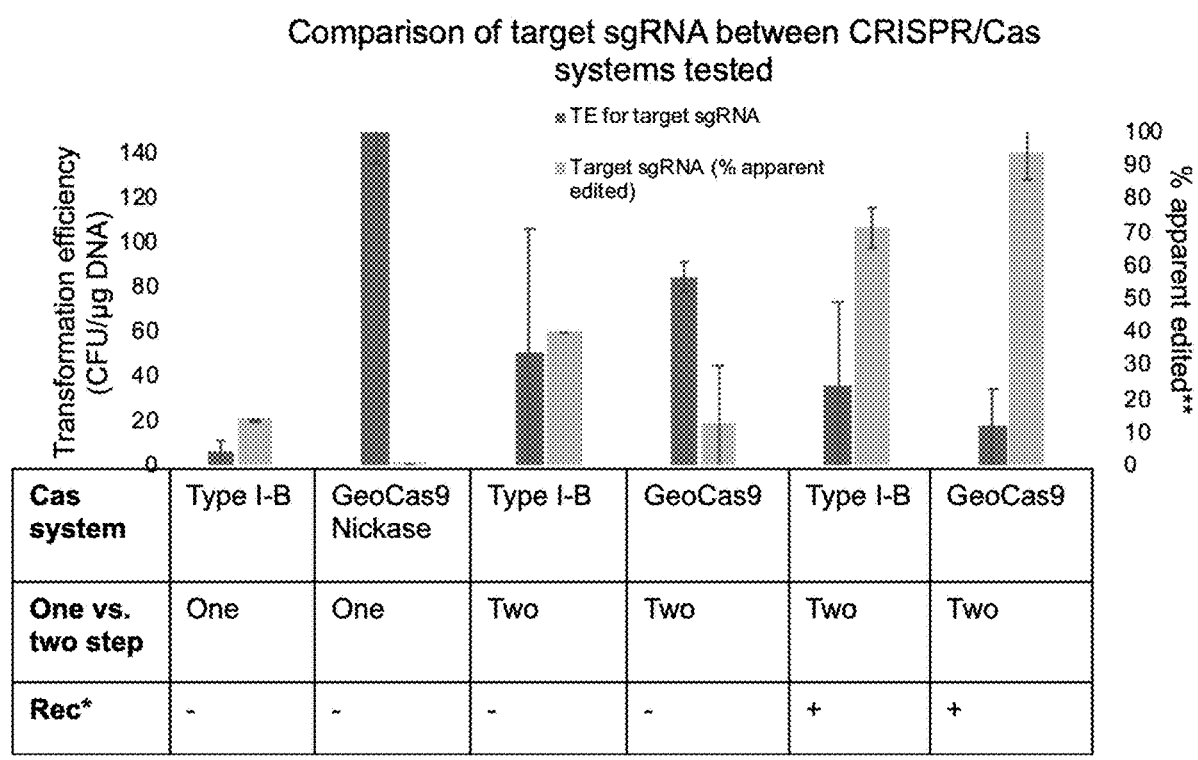
FIG. 4B is a graph showing a summary of transformation efficiency (TE) and percent apparent genomes edited for the target sgRNA for the CRISPR/Cas systems tested.

There are two important metrics to consider when evaluating the usefulness of a gene editing tool. One metric is the total number of correct transformants, the other is the fraction of correct transformants (FIG. 4B). Ideally, both would be achieved simultaneously, however there are some cases where one or the other is more important. In the absence of both recombinases and targeting sgRNAs, only a single colony in one replicate was correct. This low rate of background recombination is expected, and much too low to be useful for genetic engineering. Introducing recombinases resulted in a large improvement with an average of 14-18 correct transformants (per µg DNA). In the complete system, with both recombinases and the target sgRNA, the Type I-B system had 27 correct colonies, and the Type II system had 16 correct colonies. However the Type I-B system only had 71% correct, whereas it was 94% for the Type II system (FIG. 4B).

Given the large variability of transformation efficiency, the relatively small differences between these numbers is likely due to random variation, however to maximize the number of correct colonies (e.g. because of a need to identify a rare mutant), the Type I-B system might be preferred. On the other hand, for minimization of colony screening, the Type II system might be preferred due to its higher fraction of correct colonies. Other considerations include the choice of PAM sequence. The Type I-B system allows for easy multiplexing and its T-rich, 3 nucleotide PAM sequence is found frequently in the C. thermocellum genome. The Type II GeoCas9 has a more complex PAM sequence that could limit the choice of editing locations.

The maximum transformation efficiency of C. thermocellum is about $10^5$ CFU/ug DNA, however for the 2-step system, the second transformation frequently had an efficiency of $10^1$-$10^2$ CFU/ug DNA. This may be a result from transforming two plasmids with the same origin of replication (pNW33N). The lower transformation efficiency for the Type II system may be related to its overall toxicity. This is a frequent observation with heterologous expression of cas9 genes and may be due to off-target cutting. The higher level of background colonies in the Type I-B system (compared to the Type II system) may be due to mutations in the cas operon. The Type II system avoids the problem of cas9 mutations because the cas9 is on a multi-copy plasmid, along with the sgRNA.

In addition to the low transformation efficiency with the two-plasmid system, the Neomyocin selection has historically been an unreliable selectable marker in C. thermocellum, since the neo gene only confers a 2 to 4-fold increase in Neomycin resistance. Based on the high killing during the toxicity assay, the high background observed during the two-plasmid system may be due to the weak neomycin selection. Nonetheless, by combining the thermophilic CRISPR/Cas system (either Type I-B or Type II) with the recombinases, a new tool that allows for efficient CRISPR/Cas genome editing has been developed.

A heterologous Type II and native Type I-B CRISPR/Cas genome editing systems in the industrially relevant thermophile C. thermocellum have been developed. Both the Type II GeoCas9 and engineered Type I-B system are extremely efficient at CRISPR-mediated killing. However, a one-step CRISPR/Cas genome editing system resulted in very low genome editing outputs. The one-step system might prove less useful as a tool in certain contexts, likely due to low homologous recombination in C. thermocellum. Expressing Exo/Beta homologs from A. caldus greatly increases homologous recombination in C. thermocellum and overcomes limitations of the one-step system. By combining a thermophilic CRISPR system (either Type I-B or Type II) with recombinases via a two-step protocol, a new tool was developed that allows for efficient CRISPR/Cas genome editing. Overall, improved genome editing efficiency from 14% to 70% for the Type I-B system and from 0.21% to 94% for the Type II system was observed. Both systems enable strains to be constructed in about half the time (2 weeks) compared to traditional C. thermocellum strain construction (4 weeks). The present invention provides efficient editing tools that combine CRISPR/Cas and recombineering for rapid genome editing in C. thermocellum. These tools will be useful in other thermophilic microbes.

Glossary of Claim Terms

As used throughout the entire application, the terms "a" and "an" are used in the sense that they mean "at least one", "at least a first", "one or more" or "a plurality" of the referenced components or steps, unless the context clearly dictates otherwise. For example, the term "a cell" includes a plurality of cells, including mixtures thereof.

The term "and/or" wherever used herein includes the meaning of "and", "or" and "all or any other combination of the elements connected by said term".

The term "about" or "approximately" as used herein means within 20%, preferably within 10%, and more preferably within 5% of a given value or range.

Notwithstanding that the numerical ranges and parameters setting forth the broad scope of the disclosure are approximations, the numerical values set forth in the specific examples are reported as precisely as possible. Any numerical value, however, inherently contain certain errors necessarily resulting from the standard deviation found in their respective testing measurements. Furthermore, when numerical ranges of varying scope are set forth herein, it is contemplated that any combination of these values inclusive of the recited values may be used.

As used herein, the term "comprising" is intended to mean that the products, compositions and methods include the referenced components or steps, but not excluding others. "Consisting essentially of" when used to define products, compositions and methods, shall mean excluding other components or steps of any essential significance. Thus, a composition consisting essentially of the recited components would not exclude trace contaminants and pharmaceutically acceptable carriers. "Consisting of" shall mean excluding more than trace elements of other components or steps.

The term "Cas9" or "Cas9 nuclease" refers to an RNA-guided nuclease comprising a Cas9 protein, or a fragment thereof. A Cas9 nuclease is also referred to sometimes as a CRISPR (clustered regularly interspaced short palindromic repeat)-associated nuclease. CRISPR is an adaptive immune system that provides protection against mobile genetic elements (e.g., viruses, transposable elements and conjugative plasmids). CRISPR clusters contain spacers, sequences complementary to antecedent mobile elements, and target invading nucleic acids.

The term "consensus sequence," as used herein in the context of nucleic acid sequences, refers to a calculated sequence representing the most frequent nucleotide residues found at each position in a plurality of similar sequences. Typically, a consensus sequence is determined by sequence alignment in which similar sequences are compared to each other and similar sequence motifs are calculated. In the context of nuclease target site sequences, a consensus sequence of a nuclease target site may, in some embodiments, be the sequence most frequently bound, or bound with the highest affinity, by a given nuclease. With respect to RNA-programmable nuclease (e.g., Cas9) target site sequences, the consensus sequence may, in some embodiments, be the sequence or region to which a gRNA, or a plurality of gRNAs, is expected or designed to bind, e.g., based on complementary base pairing.

The term "effective amount," as used herein, refers to an amount of a biologically active agent that is sufficient to elicit a desired biological response. For example, in some embodiments, an effective amount of a nuclease may refer to the amount of the nuclease that is sufficient to induce cleavage of a target site specifically bound and cleaved by the nuclease. As will be appreciated by the skilled artisan, the effective amount of an agent, e.g., a nuclease, a hybrid protein, or a polynucleotide, may vary depending on various factors as, for example, on the desired biological response, the specific allele, genome, target site, cell, or tissue being targeted, and the agent being used.

The term "nuclease," as used herein, refers to an agent, for example a protein or a small molecule, capable of cleaving a phosphodiester bond connecting nucleotide residues in a nucleic acid molecule. In some embodiments, a nuclease is a protein, e.g., an enzyme that can bind a nucleic acid molecule and cleave a phosphodiester bond connecting nucleotide residues within the nucleic acid molecule. A nuclease may be an endonuclease, cleaving a phosphodiester bonds within a polynucleotide chain, or an exonuclease, cleaving a phosphodiester bond at the end of the polynucleotide chain. In some embodiments, a nuclease is a site-specific nuclease, binding and/or cleaving a specific phosphodiester bond within a specific nucleotide sequence, which is also referred to herein as the "recognition sequence," the "nuclease target site," or the "target site." In some embodiments, a nuclease is a RNA-guided (i.e., RNA-programmable) nuclease, which complexes with (e.g., binds with) an RNA having a sequence that complements a target site, thereby providing the sequence specificity of the nuclease.

The terms "polynucleotide" and "nucleic acid," used interchangeably herein, refer to a polymeric form of nucleotides of any length, either ribonucleotides or deoxynucleotides. Thus, this term includes, but is not limited to, single-, double-, or multi-stranded DNA or RNA, genomic DNA, cDNA, DNA-RNA hybrids, or a polymer comprising purine and pyrimidine bases or other natural, chemically or biochemically modified, non-natural, or derivatized nucleotide bases. The terms "polynucleotide" and "nucleic acid" should be understood to include, as applicable to the embodiment being described, single-stranded (such as sense or antisense) and double-stranded polynucleotides.

The terms "peptide," "polypeptide," and "protein" are used interchangeably herein, and refer to a polymeric form of amino acids of any length, which can include coded and non-coded amino acids, chemically or biochemically modified or derivatized amino acids, and polypeptides having modified peptide backbones.

As used herein the term "isolated" is meant to describe a polynucleotide, a polypeptide, or a cell that is in an environment different from that in which the polynucleotide, the polypeptide, or the cell naturally occurs. An isolated genetically modified host cell may be present in a mixed population of genetically modified host cells.

"Recombinant," as used herein, means that a particular nucleic acid (DNA or RNA) or protein is the product of various combinations of cloning, restriction, and/or ligation steps resulting in a construct having a structural coding or non-coding sequence distinguishable from endogenous nucleic acids found in natural systems. Thus, e.g., the term "recombinant" polynucleotide or "recombinant" nucleic acid refers to one which is not naturally occurring, e.g., is made by the artificial combination of two otherwise separated segments of sequence through human intervention. This artificial combination is often accomplished by either chemical synthesis means, or by the artificial manipulation of isolated segments of nucleic acids, e.g., by genetic engineering techniques. Such is usually done to replace a codon with a redundant codon encoding the same or a conservative amino acid, while typically introducing or removing a sequence recognition site. Alternatively, it is performed to join together nucleic acid segments of desired functions to generate a desired combination of functions. This artificial combination is often accomplished by either chemical synthesis means, or by the artificial manipulation of isolated segments of nucleic acids, e.g., by genetic engineering techniques.

"Operably linked" refers to a juxtaposition wherein the components so described are in a relationship permitting them to function in their intended manner. For instance, a promoter is operably linked to a nucleotide sequence (e.g., a protein coding sequence, e.g., a sequence encoding an mRNA; a non protein coding sequence, e.g., a sequence encoding a non-coding RNA (ncRNA) such as a Cas9 guide RNA; and the like) if the promoter affects its transcription and/or expression. The relationship can also be referred to in the reverse and retain the same meaning. For example, a nucleotide sequence of interest can be said to be operably linked to a promoter. As used herein, the terms "heterologous promoter" and "heterologous control regions" refer to promoters and other control regions that are not normally associated with a particular nucleic acid in nature. For example, a "transcriptional control region heterologous to a coding region" is a transcriptional control region that is not normally associated with the coding region in nature.

"Heterologous," as used herein, means a nucleotide or polypeptide sequence that is not found in the native nucleic acid or protein, respectively. For example, a variant Cas9 protein can be a chimeric variant Cas9 protein that includes a heterologous amino acid sequence (e.g., a fusion partner).

The term "naturally-occurring" as used herein as applied to a nucleic acid, a protein, a cell, or an organism, refers to a nucleic acid, protein, cell, or organism that is found in nature. For example, a polypeptide or polynucleotide sequence that is present in an organism (including viruses) that can be isolated from a source in nature and which has not been intentionally modified by a human in the laboratory is naturally occurring.

The terms "target nucleic acid," and "target genome," as used herein in the context of nucleases, refer to a nucleic acid molecule or a genome, respectively, that comprises at least one target site of a given nuclease.

The term "target site," used herein interchangeably with the term "nuclease target site," refers to a sequence within a nucleic acid molecule that is bound and cleaved by a nuclease.

The advantages set forth above, and those made apparent from the foregoing description, are efficiently attained. Since certain changes may be made in the above construction without departing from the scope of the invention, it is intended that all matters contained in the foregoing description or shown in the accompanying drawings shall be interpreted as illustrative and not in a limiting sense.

All references cited in the present application are incorporated in their entirety herein by reference to the extent not inconsistent herewith.

It will be seen that the advantages set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween. Now that the invention has been described,

TABLE 1

Description of Strains and Plasmids.

| Strain | Organism | Description | Accession Number |
|---|---|---|---|
| DSM1313 | *Clostridium thermocellum* | wild type | CP002416 |
| LL1299 | *Clostridium thermocellum* | DSM1313 ΔhptΔ0478 | |
| LL1584 | *Clostridium thermocellum* | LL1299 Peno-Cas operon | SRP164871 |
| LL1585 | *Clostridium thermocellum* | LL1299 P#0815-Cas operon | SRP164872 |
| LL1586 | *Clostridium thermocellum* | LL1299 PTsac#0068-Cas operon | SRP164875 |
| LL1587 | *Clostridium thermocellum* | LL1299 PTsac#2130-Cas operon | SRP164873 |
| LL1588 | *Clostridium thermocellum* | LL1299 PTsac#0530-Cas operon | SRP164874 |
| 61 | *Clostridium thermocellum* | LL1586 one-step escape mutant, cas5 mutation | SRP164861 |
| 62 | *Clostridium thermocellum* | LL1586 one-step escape mutant, cas3 mutation | SRP164864 |
| 63 | *Clostridium thermocellum* | LL1586 one-step escape mutant, cas8 mutation | SRP164863 |
| 67 | *Clostridium thermocellum* | LL1586 one-step escape mutant, cas5 mutation | SRP164866 |
| 70 | *Clostridium thermocellum* | LL1586 one-step escape mutant, cas5 mutation | SRP164865 |
| 71 | *Clostridium thermocellum* | LL1586 one-step escape mutant, cas8 mutation | SRP164867 |
| 72 | *Clostridium thermocellum* | LL1586 one-step escape mutant, cas8 mutation | SRP164868 |

| Plasmids | Description | crRNA/spacer sequence |
|---|---|---|
| pJEW54 | $P_{Tsac0068}$GeoCas9; $P_{Clo1313\_2638}$non-target_sgRNA | TTCCCTGGTACCTAGGAACCCG [SEQ ID NO. 1] |
| pJEW55 | $P_{Tsac0068}$GeoCas9; $P_{Clo1313\_2638}$SgRNA#1 | gggcatatttgttctggtcaag [SEQ ID NO. 2] |
| pJEW56 | $P_{Tsac0068}$GeoCas9; $P_{Clo1313\_2638}$SgRNA#2 | tcgtttcttttccgtctgcaa [SEQ ID NO. 3] |
| pJEW57 | $P_{Tsac0068}$GeoCas9; $P_{Clo1313\_2638}$SgRNA#3 | CGGGTTGACTGTCAGGGCATCC [SEQ ID NO. 4] |
| pJEW63 | $P_{Tsac0068}$ThermoCas9; $P_{Clo1313\_2638}$non-target_sgRNA | TGTCATAGCGCTAGATCCGG [SEQ ID NO. 5] |
| pJEW64 | $P_{Tsac0068}$ThermoCas9; $P_{Clo1313\_2638}$SgRNA#1 | gcatatttgttctggtcaag [SEQ ID NO. 6] |
| pJEW70 | $P_{Tsac0068}$AceCas9; $P_{Clo1313\_2638}$non-target_sgRNA | CTTCCGCTGAGACTCCCCTTACAC [SEQ ID NO. 7] |
| pJEW71 | $P_{Tsac0068}$AceCas9; $P_{Clo1313\_2638}$SgRNA#1 | ggattagaccctaaaattgaatat [SEQ ID NO. 8] |
| pJEW72 | $P_{Tsac0068}$AceCas9; $P_{Clo1313\_2638}$sgRNA#2 | caagatacgggttgactgtcaggg [SEQ ID NO. 9] |

TABLE 1-continued

Description of Strains and Plasmids.

| | | |
|---|---|---|
| pJEW68 | $P_{Tsac0068}$GeoCas9; $P_{Clo1313\_2638}$ non-target_sgRNA_HA | TTCCCTGGTACCTAGGAACCCG [SEQ ID NO. 10] |
| pJEW69 | $P_{Tsac0068}$GeoCas9; $P_{Clo1313\_2638}$_sgRNA#1_HA | gggcatatttgttctggtcaag [SEQ ID NO. 11] |
| pJEW84 | $P_{Tsac0068}$GeoCas9n; $P_{Clo1313\_2638}$ non-target_sgRNA_HA | TTCCCTGGTACCTAGGAACCCG [SEQ ID NO. 12] |
| pJEW85 | $P_{Tsac0068}$GeoCas9n; $P_{Clo1313\_2638}$sgRNA#1_HA | gggcatatttgttctggtcaag [SEQ ID NO. 13] |
| pJEW112 | HA | |
| pJEW106 | $P_{Tsac530}$A.caldusBeta_Exo; HA | |
| pJEW107 | $P_{Tsac530}$C.stercorariumRecT_RecE; HA | |
| pJEW108 | $P_{Tsac530}$GeobacillusRecT_RecE; HA | |
| pJEW136 | $P_{Tsac530}$A.caldusBeta_Exo; HA_500bp | |
| pJEW137 | $P_{Tsac530}$A.caldusBeta_Exo; HA_50bp | |
| pJEW117 | NeoR; $P_{Tsac0068}$GeoCas9; $P_{Clo1313\_2638}$non-target_sgRNA | TTCCCTGGTACCTAGGAACCCG [SEQ ID NO. 14] |
| pJEW111 | NeoR; $P_{Tsac0068}$GeoCas9; $P_{Clo1313\_2638}$SgRNA#1 | gggcatatttgttctggtcaag [SEQ ID NO. 15] |
| pTY11B | $P_{Clo1313\_1194}$ | ATAATGACATTTATGGTACTGTTGTGGTAATAG ACGA [SEQ ID NO. 16] |
| pTY21B | $P_{Clo1313\_1194}$ | ATAATGACATTTATGGTACTGTTGTGGTAATAG ACGA [SEQ ID NO. 17] |
| pTY32B | $P_{Clo1313\_1194}$ | ATAATGACATTTATGGTACTGTTGTGGTAATAG ACGA [SEQ ID NO. 18] |
| pTY62B | $P_{Clo1313\_1194}$ | ATAATGACATTTATGGTACTGTTGTGGTAATAG ACGA [SEQ ID NO. 19] |
| pTY11C | $P_{Clo1313\_2638}$ | ATAATGACATTTATGGTACTGTTGTGGTAATAG ACGA [SEQ ID NO. 20] |
| pTY21C | $P_{Clo1313\_2638}$ | ATAATGACATTTATGGTACTGTTGTGGTAATAG ACGA [SEQ ID NO. 21] |
| pTY32C | $P_{Clo1313\_2638}$ | ATAATGACATTTATGGTACTGTTGTGGTAATAG ACGA [SEQ ID NO. 22] |
| pTY62C | $P_{Clo1313\_2638}$ | ATAATGACATTTATGGTACTGTTGTGGTAATAG ACGA [SEQ ID NO. 23] |
| pDGO185N | pyrF targeting, deletion | CAAGTTTCATAAAACACCCTCATGCCTTCAAGG CCGT [SEQ ID NO. 24] |
| pDGO186N | pyrF targeting, deletion | TGAGATTGTTGCGGAGTATGTTGAATCATGGGG TGAA [SEQ ID NO. 25] |
| pDGO187N | pyrF target, deletion, no sgRNA control | none |
| pDGO186N-S1_nheI | pyrF target, stop codon insertion, target sgRNA | TGAGATTGTTGCGGAGTATGTTGAATCATGGGG TGAA [SEQ ID NO. 26] |
| pDGO186N-S1_CS | pyrF non-target control, stop codon insertion, non target control sgRNA | CTTGAAGGCATGAGGGTGTTTTATGAAACTTGC AAAT [SEQ ID NO. 27] |
| pDGO186NX-S1_nheI | pyrF target, stop codon insertion | none |
| pDGO186NX R-S1_nheI | pyrF target, stop codon insertion, recombinase | none |

TABLE 1-continued

Description of Strains and Plasmids.

| | | |
|---|---|---|
| pDGO186N-CS3neo | NeoR; target sgRNA | TGAGATTGTTGCGGAGTATGTTGAATCATGGGGTGAA [SEQ ID NO. 28] |
| pDGO186N-ContS-neo | NeoR; control sgRNA | CTTGAAGGCATGAGGGTGTTTTATGAAACTTGCAAAT [SEQ ID NO. 29] |

TABLE 2

Cas operon identification

| Locus ID | Position* | Genes | Cas elements | # of repeats | Repeat length |
|---|---|---|---|---|---|
| 1 | 880663 . . . 881557 | Clo1313_0765-0764 | Cas 2, Cas4 | 3 | 37 |
| 2 | 976954 . . . 982276 | | none | 81 | 30 |
| 3 | 1914892 . . . 1916668 | | none | 27 | 30 |
| 4 | 1930002 . . . 1933245 | | none | 49 | 30 |
| 5 | 3480177 . . . 3490240 | Clo1313_2969-2976 | Cas2, Cas1, Cas4, Cas3, Cas5, DevR, Cas8, Cas6 | 29 | 30 |

TABLE 3

Type I-B escape mutants

| Strain ID | Cas gene | Mutation |
|---|---|---|
| 61 | cas5 | Ile85fs |
| 62 | cas3 | Lys490fs |
| 63 | cas8 | Lys275fs |
| 67 | cas5 | Ile146fs |
| 70 | cas5 | Ile146fs |
| 71 | cas8 | Tyr515* (stop) |
| 72 | cas8 | Glu120fs |

TABLE 4

Key differences between the native Type I-B and the Type II CRISPR systems

| Feature | Native type I-B | Type II |
|---|---|---|
| Organism | Clostridium thermocellum | Geobacillus stearothermpohilus |
| Nuclease | Cas3 | Cas9 |
| PAM | 5'-TTN-3', 5'-TCD-3' | 5'-NNNNCRAA-3' |
| guide RNA | 97nt, spacer (ranges from 31-42nt), with two flanking repeats (30nt each) | 140nt, crispr/spacer RNA sequence (22nt) and tracrRNA (118nt) fused together to form a sgRNA |
| Holoenzyme | 4 proteins (cas4, cas5, cas8 and cas3) in complex with a sgRNA | One protein (Cas9) in complex with a sgRNA |

TABLE 5

One-step CRISPR/Cas genome editing results.

| Metric | Spacer | Type 1-B | Type II | Type II (nickase) |
|---|---|---|---|---|
| Transformation (CFU/µg DNA) efficiency | Non-target | 18,000 ± 7000 | 55 ± 7 | 200 ± 70 |
| | Target | 7 ± 4.2 | 0 ± 0 | 150 ± 14 |
| Percent increase phenotype | Non-target | 11 ± 2.9 | n/a | 0.03 ± 0.01 |

TABLE 5-continued

One-step CRISPR/Cas genome editing results.

| Metric | Spacer | Type 1-B | Type II | Type II (nickase) |
|---|---|---|---|---|
| observed in 5-FOA$^R$ | Target | 14 ± 3.4 | n/a | 0.21 ± 0.07 |
| CRISPR fold change* | | 1.3 ± 0.13 | n/a | 7.3 ± 0.19 |

*Percent increase observed in 5-FOA$^R$ phenotype/X = (Cfus on Tm + 5FOA)/(Cfus on Tm)
**CRISPR fold change based off of 5-FOA$^R$ = X for target gRNA/X for non-target gRNA

TABLE 6

Two step +/- recombineering machinery results.

| Metric | Spacer | Type I-B | Type 1-B + rec* | Type II | Type II + rec* |
|---|---|---|---|---|---|
| Transformation (CFU/µg DNA) efficiency | Non-target | 210 ± 260 | 150 ± 53 | 41 ± 41 | 31 ± 29 |
| | Target | 51 ± 55 | 36 ± 38 | 85 ± 7 | 18 ± 17 |
| Percent of colonies correctly edited* | Non-target | 0 ± 0 | 0 ± 0 | 4 ± 6 | 55 ± 18 |
| | Target | 40 ± 0 | 71 ± 6 | 13 ± 18 | 94 ± 9 |
| CRISPR fold change** | | 40 ± 0 | 71 ± 0.0 | 8.5 ± 2 | 1.7 ± 0.12 |

*Percent colonies edited (X): Percentage of correct colonies verified by restriction digest.
**CRISPR fold change based off of percentage correct colonies = X for target sgRNA/X for non-target sgRNA

TABLE 7

PAM3 depletion PAM seq

| | pDGO1 80 | pDGO1 82 | pDGO1 83 no sp |
|---|---|---|---|
| AAA | 1.32 | 1.31 | 0.98 |
| AAC | 1.50 | 1.45 | 1.13 |
| AAG | 1.44 | 1.35 | 0.93 |
| AAT | 1.46 | 1.32 | 1.04 |
| ACA | 1.31 | 1.20 | 0.89 |
| ACC | 1.51 | 1.32 | 1.02 |
| ACG | 1.66 | 1.24 | 0.95 |
| ACT | 1.41 | 1.24 | 1.05 |
| AGA | 1.28 | 1.23 | 0.90 |

TABLE 7-continued

| PAM3 depletion PAM seq | | | |
|---|---|---|---|
| | pDGO1 80 | pDGO1 82 | pDGO1 83 no sp |
| AGC | 1.28 | 1.33 | 0.95 |
| AGG | 1.64 | 1.36 | 0.96 |
| AGT | 1.40 | 1.38 | 0.99 |
| ATA | 0.81 | 0.94 | 1.09 |
| ATC | 1.32 | 1.28 | 1.08 |
| ATG | 1.36 | 1.24 | 1.02 |
| ATT | 0.54 | 1.24 | 1.02 |
| CAA | 1.21 | 1.09 | 1.06 |
| CAC | 1.42 | 1.20 | 1.07 |
| CAG | 1.34 | 1.32 | 0.98 |
| CAT | 1.28 | 1.25 | 1.00 |
| CCA | 0.37 | 0.54 | 1.03 |
| CCC | 1.56 | 1.33 | 1.02 |
| CCG | 0.99 | 1.20 | 0.97 |
| CCT | 1.15 | 1.29 | 0.97 |
| CGA | 1.09 | 1.14 | 1.14 |
| CGC | 1.43 | 1.28 | 1.02 |
| CGG | 1.48 | 1.31 | 0.94 |
| CGT | 1.34 | 1.26 | 1.00 |
| CTA | 0.22 | 0.22 | 1.07 |
| CTC | 1.21 | 1.25 | 1.09 |
| CTG | 0.24 | 0.35 | 0.92 |
| CTT | 0.25 | 0.92 | 1.02 |
| GAA | 1.32 | 1.32 | 0.96 |
| GAC | 1.46 | 1.23 | 1.02 |
| GAG | 1.37 | 1.35 | 0.92 |
| GAT | 1.38 | 1.32 | 1.01 |
| GCA | 1.23 | 1.27 | 1.01 |
| GCC | 1.39 | 1.33 | 1.00 |
| GCG | 1.52 | 1.29 | 0.98 |
| GCT | 1.38 | 1.23 | 0.94 |
| GGA | 1.31 | 1.24 | 0.94 |
| GGC | 1.34 | 1.25 | 0.97 |
| GGG | 1.58 | 1.31 | 0.92 |
| GGT | 1.33 | 1.33 | 1.00 |
| GTA | 0.73 | 0.98 | 1.10 |
| GTC | 1.27 | 1.31 | 0.99 |
| GTG | 1.41 | 1.28 | 0.99 |
| GTT | 0.23 | 1.31 | 1.09 |
| TAA | 0.21 | 0.21 | 1.13 |
| TAC | 1.26 | 1.02 | 1.09 |
| TAG | 0.22 | 0.54 | 0.94 |
| TAT | 0.33 | 0.67 | 1.07 |
| TCA | 0.21 | 0.21 | 1.07 |
| TCC | 0.78 | 0.79 | 1.05 |
| TCG | 0.23 | 0.22 | 1.06 |
| TCT | 0.22 | 0.21 | 1.10 |
| TGA | 0.22 | 0.21 | 1.01 |
| TGC | 1.36 | 1.29 | 1.07 |
| TGG | 0.24 | 0.40 | 0.96 |
| TGT | 0.27 | 0.48 | 1.02 |
| TTA | 0.20 | 0.19 | 0.99 |
| TTC | 0.24 | 0.22 | 1.00 |
| TTG | 0.23 | 0.21 | 1.02 |
| TTT | 0.21 | 0.22 | 1.04 |

What is claimed is:

1. A system for the engineering of a thermophilic bacterial species comprising:
   a first expression vector plasmid comprising a repair template and encoding recombinases, wherein the recombinases are exo/beta homologs from *Acidithiobacillus caldus*; and
   a second expression vector plasmid encoding an sgRNA and a thermophilic cas9 variant.

2. The system according to claim 1 wherein the thermophilic cas9 variant is a nickase cas9.

3. The system according to claim 1 wherein the thermophilic cas9 variant is GeoCas9 derived from *Geobacillus stearothermophilus*.

4. The system according to claim 1 further comprising a population of *Clostridium thermocellum* bacteria.

5. A method of engineering a thermophilic bacteria population comprising the steps of:
   transfecting the bacteria population with a first expression vector plasmid comprising exo/beta recombineering genes from *Acidithiobacillus caldus* and a repair template;
   performing one or more passages of the bacteria, whereby the passages allow for recombination between the repair template and the genome of bacteria in the bacterial population; and
   transfecting the bacteria population with a second expression vector plasmid encoding an sgRNA and a thermophilic cas9 variant.

6. The method according to claim 5, wherein the thermophilic cas9 variant is a nickase cas9.

7. The method according to claim 5, wherein the thermophilic cas9 variant is GeoCas9 derived from *Geobacillus stearothermophilus*.

8. The method according to claim 5, wherein the bacteria population is a population of *Clostridium thermocellum* bacteria.

* * * * *

SEQUENCE LISTING

```
<160> NUMBER OF SEQ ID NOS: 29

<210> SEQ ID NO 1
<211> LENGTH: 22
<212> TYPE: DNA
<213> ORGANISM: Artificial Sequence
<220> FEATURE:
<223> OTHER INFORMATION: crRNA/spacer sequence

<400> SEQUENCE: 1
ttccctggta cctaggaacc cg                                           22

<210> SEQ ID NO 2
<211> LENGTH: 22
<212> TYPE: DNA
<213> ORGANISM: Artificial Sequence
<220> FEATURE:
<223> OTHER INFORMATION: crRNA/spacer sequence

<400> SEQUENCE: 2
gggcatattt gttctggtca ag                                           22

<210> SEQ ID NO 3
<211> LENGTH: 22
<212> TYPE: DNA
<213> ORGANISM: Artificial Sequence
<220> FEATURE:
<223> OTHER INFORMATION: crRNA/spacer sequence

<400> SEQUENCE: 3
tcgtttcttt ttccgtctgc aa                                           22

<210> SEQ ID NO 4
<211> LENGTH: 22
<212> TYPE: DNA
```

```
<213> ORGANISM: Artificial Sequence
<220> FEATURE:
<223> OTHER INFORMATION: crRNA/spacer sequence

<400> SEQUENCE: 4
cgggttgact gtcagggcat cc                                          22

<210> SEQ ID NO 5
<211> LENGTH: 20
<212> TYPE: DNA
<213> ORGANISM: Artificial Sequence
<220> FEATURE:
<223> OTHER INFORMATION: crRNA/spacer sequence

<400> SEQUENCE: 5
tgtcatagcg ctagatccgg                                             20

<210> SEQ ID NO 6
<211> LENGTH: 20
<212> TYPE: DNA
<213> ORGANISM: Artificial Sequence
<220> FEATURE:
<223> OTHER INFORMATION: crRNA/spacer sequence

<400> SEQUENCE: 6
gcatatttgt tctggtcaag                                             20

<210> SEQ ID NO 7
<211> LENGTH: 24
<212> TYPE: DNA
<213> ORGANISM: Artificial Sequence
<220> FEATURE:
<223> OTHER INFORMATION: crRNA/spacer sequence

<400> SEQUENCE: 7
cttccgctga gactcccctt acac                                        24

<210> SEQ ID NO 8
<211> LENGTH: 24
<212> TYPE: DNA
<213> ORGANISM: Artificial Sequence
<220> FEATURE:
<223> OTHER INFORMATION: crRNA/spacer sequence

<400> SEQUENCE: 8
ggattagacc ctaaaattga atat                                        24

<210> SEQ ID NO 9
<211> LENGTH: 24
<212> TYPE: DNA
<213> ORGANISM: Artificial Sequence
<220> FEATURE:
<223> OTHER INFORMATION: crRNA/spacer sequence

<400> SEQUENCE: 9
caagatacgg gttgactgtc aggg                                        24

<210> SEQ ID NO 10
<211> LENGTH: 22
<212> TYPE: DNA
<213> ORGANISM: Artificial Sequence
<220> FEATURE:
<223> OTHER INFORMATION: crRNA/spacer sequence

<400> SEQUENCE: 10
ttccctggta cctaggaacc cg                                          22
```

```
<210> SEQ ID NO 11
<211> LENGTH: 22
<212> TYPE: DNA
<213> ORGANISM: Artificial Sequence
<220> FEATURE:
<223> OTHER INFORMATION: crRNA/spacer sequence

<400> SEQUENCE: 11
gggcatattt gttctggtca ag                                              22

<210> SEQ ID NO 12
<211> LENGTH: 22
<212> TYPE: DNA
<213> ORGANISM: Artificial Sequence
<220> FEATURE:
<223> OTHER INFORMATION: crRNA/spacer sequence

<400> SEQUENCE: 12
ttccctggta cctaggaacc cg                                              22

<210> SEQ ID NO 13
<211> LENGTH: 22
<212> TYPE: DNA
<213> ORGANISM: Artificial Sequence
<220> FEATURE:
<223> OTHER INFORMATION: crRNA/spacer sequence

<400> SEQUENCE: 13
gggcatattt gttctggtca ag                                              22

<210> SEQ ID NO 14
<211> LENGTH: 22
<212> TYPE: DNA
<213> ORGANISM: Artificial Sequence
<220> FEATURE:
<223> OTHER INFORMATION: crRNA/spacer sequence

<400> SEQUENCE: 14
ttccctggta cctaggaacc cg                                              22

<210> SEQ ID NO 15
<211> LENGTH: 22
<212> TYPE: DNA
<213> ORGANISM: Artificial Sequence
<220> FEATURE:
<223> OTHER INFORMATION: crRNA/spacer sequence

<400> SEQUENCE: 15
gggcatattt gttctggtca ag                                              22

<210> SEQ ID NO 16
<211> LENGTH: 37
<212> TYPE: DNA
<213> ORGANISM: Artificial Sequence
<220> FEATURE:
<223> OTHER INFORMATION: crRNA/spacer sequence

<400> SEQUENCE: 16
ataatgacat ttatggtact gttgtggtaa tagacga                              37

<210> SEQ ID NO 17
<211> LENGTH: 37
<212> TYPE: DNA
<213> ORGANISM: Artificial Sequence
<220> FEATURE:
```

<223> OTHER INFORMATION: crRNA/spacer sequence

<400> SEQUENCE: 17
ataatgacat ttatggtact gttgtggtaa tagacga                              37

<210> SEQ ID NO 18
<211> LENGTH: 37
<212> TYPE: DNA
<213> ORGANISM: Artificial Sequence
<220> FEATURE:
<223> OTHER INFORMATION: crRNA/spacer sequence

<400> SEQUENCE: 18
ataatgacat ttatggtact gttgtggtaa tagacga                              37

<210> SEQ ID NO 19
<211> LENGTH: 37
<212> TYPE: DNA
<213> ORGANISM: Artificial Sequence
<220> FEATURE:
<223> OTHER INFORMATION: crRNA/spacer sequence

<400> SEQUENCE: 19
ataatgacat ttatggtact gttgtggtaa tagacga                              37

<210> SEQ ID NO 20
<211> LENGTH: 37
<212> TYPE: DNA
<213> ORGANISM: Artificial Sequence
<220> FEATURE:
<223> OTHER INFORMATION: crRNA/spacer sequence

<400> SEQUENCE: 20
ataatgacat ttatggtact gttgtggtaa tagacga                              37

<210> SEQ ID NO 21
<211> LENGTH: 37
<212> TYPE: DNA
<213> ORGANISM: Artificial Sequence
<220> FEATURE:
<223> OTHER INFORMATION: crRNA/spacer seqeunce

<400> SEQUENCE: 21
ataatgacat ttatggtact gttgtggtaa tagacga                              37

<210> SEQ ID NO 22
<211> LENGTH: 37
<212> TYPE: DNA
<213> ORGANISM: Artificial Sequence
<220> FEATURE:
<223> OTHER INFORMATION: crRNA/spacer sequence

<400> SEQUENCE: 22
ataatgacat ttatggtact gttgtggtaa tagacga                              37

<210> SEQ ID NO 23
<211> LENGTH: 37
<212> TYPE: DNA
<213> ORGANISM: Artificial Sequence
<220> FEATURE:
<223> OTHER INFORMATION: crRNA/spacer sequence

<400> SEQUENCE: 23
ataatgacat ttatggtact gttgtggtaa tagacga                              37

```
<210> SEQ ID NO 24
<211> LENGTH: 37
<212> TYPE: DNA
<213> ORGANISM: Artificial Sequence
<220> FEATURE:
<223> OTHER INFORMATION: crRNA/spacer sequnce

<400> SEQUENCE: 24
caagtttcat aaaacaccct catgccttca aggccgt                              37

<210> SEQ ID NO 25
<211> LENGTH: 37
<212> TYPE: DNA
<213> ORGANISM: Artificial Sequence
<220> FEATURE:
<223> OTHER INFORMATION: crRNA/spacer sequence

<400> SEQUENCE: 25
tgagattgtt gcggagtatg ttgaatcatg gggtgaa                              37

<210> SEQ ID NO 26
<211> LENGTH: 37
<212> TYPE: DNA
<213> ORGANISM: Artificial Sequence
<220> FEATURE:
<223> OTHER INFORMATION: crRNA/spacer sequence

<400> SEQUENCE: 26
tgagattgtt gcggagtatg ttgaatcatg gggtgaa                              37

<210> SEQ ID NO 27
<211> LENGTH: 37
<212> TYPE: DNA
<213> ORGANISM: Artificial Sequence
<220> FEATURE:
<223> OTHER INFORMATION: crRNA/spacer sequence

<400> SEQUENCE: 27
cttgaaggca tgagggtgtt ttatgaaact tgcaaat                              37

<210> SEQ ID NO 28
<211> LENGTH: 37
<212> TYPE: DNA
<213> ORGANISM: Artificial Sequence
<220> FEATURE:
<223> OTHER INFORMATION: crRNA/spacer sequence

<400> SEQUENCE: 28
tgagattgtt gcggagtatg ttgaatcatg gggtgaa                              37

<210> SEQ ID NO 29
<211> LENGTH: 37
<212> TYPE: DNA
<213> ORGANISM: Artificial Sequence
<220> FEATURE:
<223> OTHER INFORMATION: crRNA/spacer sequence

<400> SEQUENCE: 29
cttgaaggca tgagggtgtt ttatgaaact tgcaaat                              37
```